United States Patent
Bar-Joseph et al.

(10) Patent No.: US 12,374,426 B2
(45) Date of Patent: Jul. 29, 2025

(54) PREDICTING mRNA PROPERTIES USING LARGE LANGUAGE TRANSFORMER MODELS

(71) Applicant: Sanofi, Paris (FR)

(72) Inventors: Ziv Bar-Joseph, Cambridge, MA (US); Sven Frederik Jager, Frankfurt am Main (DE); Sizhen Li, Cambridge, MA (US); Saeed Moayedpour, Cambridge, MA (US)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 18/785,864

(22) Filed: Jul. 26, 2024

(65) Prior Publication Data

US 2025/0037795 A1    Jan. 30, 2025

Related U.S. Application Data

(60) Provisional application No. 63/648,338, filed on May 16, 2024, provisional application No. 63/516,226, filed on Jul. 28, 2023.

(30) Foreign Application Priority Data

May 16, 2024    (EP) .................... 24305758

(51) Int. Cl.
*G16B 30/00* (2019.01)
*G16B 20/00* (2019.01)
*G16B 40/20* (2019.01)

(52) U.S. Cl.
CPC ............. *G16B 30/00* (2019.02); *G16B 20/00* (2019.02); *G16B 40/20* (2019.02)

(58) Field of Classification Search
None
See application file for complete search history.

(56) References Cited

FOREIGN PATENT DOCUMENTS

CN    111951891 B    11/2022

OTHER PUBLICATIONS

Castillo-Hair, S. M., & Seelig, G. (2021). Machine learning for designing next-generation mRNA therapeutics. Accounts of Chemical Research, 55(1), 24-34. (Year: 2021).*
Leppek, K., Byeon, G. W., Kladwang, W., Wayment-Steele, H. K., Kerr, C. H., Xu, A. F., . . . & Das, R. (2022). Combinatorial optimization of mRNA structure, stability, and translation for RNA-based therapeutics. Nature communications, 13(1), 1536. (Year: 2022).*

(Continued)

*Primary Examiner* — Karlheinz R. Skowronek
*Assistant Examiner* — Noah A. Auger
(74) *Attorney, Agent, or Firm* — Fish & Richardson P.C.

(57) ABSTRACT

Methods, computer systems, and apparatus, including computer programs encoded on computer storage media, for predicting mRNA properties. The system obtains data representing a codon sequence of the mRNA molecule, generates an input token vector by numerically encoding the codon sequence, and generates an embedded feature vector by processing the input token vector using an embedding machine-learning model having a first set of model parameters.

29 Claims, 10 Drawing Sheets

(56) References Cited

OTHER PUBLICATIONS

Ouranidis, A., Vavilis, T., Mandala, E., Davidopoulou, C., Stamoula, E., Markopoulou, C. K., . . . & Kachrimanis, K. (2021). mRNA therapeutic modalities design, formulation and manufacturing under pharma 4.0 principles. Biomedicines, 10(1), 50. (Year: 2021).*

Chaudhary, N., Weissman, D., & Whitehead, K. A. (2021). mRNA vaccines for infectious diseases: principles, delivery and clinical translation. Nature reviews Drug discovery, 20(11), 817-838. (Year: 2021).*

He, L., Zhang, S., Wu, L., Xia, H., Ju, F., Zhang, H., . . . & Liu, T. Y. (2021). Pre-training co-evolutionary protein representation via a pairwise masked language model. arXiv preprint arXiv:2110.15527. (Year: 2021).*

Song, B., Li, Z., Lin, X., Wang, J., Wang, T., & Fu, X. (2021). Pretraining model for biological sequence data. Briefings in functional genomics, 20(3), 181-195. (Year: 2021).*

Wei, L., Liao, M., Gao, Y., Ji, R., He, Z., & Zou, Q. (2013). Improved and promising identification of human microRNAs by incorporating a high-quality negative set. IEEE/ACM transactions on computational biology and bioinformatics, 11(1), 192-201. (Year: 2013).*

Cao, Y., & Shen, Y. (2021). TALE: Transformer-based protein function Annotation with joint sequence—Label Embedding. Bioinformatics, 37(18), 2825-2833. (Year: 2021).*

International Search Report and Written Opinion in International Appln. No. PCT/EP2024/071375, mailed on Oct. 23, 2024, 24 pages.

International Search Report and Written Opinion in International Appln. No. PCT/EP2024/071380, mailed on Oct. 24, 2024, 22 pages.

Akiyama et al., "Informative RNA base embedding for RNA structural alignment and clustering by deep representation learning," NAR Genomics and Bioinformatics, Feb. 22, 2022, 4(1):1-11.

Chen et al., "Interpretable RNA foundation model from unannotated data for highly accurate RNA structure and function predictions," CoRR, Submitted on May 13, 2022, arXiv:2204.00300v2, 25 pages.

Constant et al., "Deep learning-based codon optimization with large-scale synonymous variant datasets enables generalized tunable protein expression," BioRxiv, Feb. 12, 2023, 56 pages.

Agarwal et al., "Predicting mRNA abundance directly from genomic sequence using deep convolutional neural networks," Cell Reports, May 19, 2020, 31(7).

Agarwal et al., "The genetic and biochemical determinants of mRNA degradation rates in mammals," Genome Biology, Nov. 23, 2022, 23(1):245.

Ahmad et al., "Immune tolerance vs. immune resistance: the interaction between host and pathogens in infectious diseases," Frontiers in Veterinary Science, Mar. 29, 2022, 9:827407.

Al-Hawash et al., "Strategies of codon optimization for high-level heterologous protein expression in microbial expression systems," Gene Reports, Dec. 1, 2017, 9:46-53.

Aw et al., "In Vivo Mapping of Eukaryotic RNA Interactomes Reveals Principles of Higher-Order Organization and Regulation," Molecular Cell, May 19, 2016, 62(4):603-617.

Bepler et al., "Learning the protein language: Evolution, structure, and function," Cell Systems, Jun. 16, 2021, 12(6):654-669.

Chen et al., "Interpretable RNA Foundation Model from Unannotated Data for Highly Accurate RNA Structure and Function Predictions," CoRR, Submitted on Apr. 1, 2022, arXiv:2204.00300v1, 23 pages.

Devlin et al., "BERT: Pre-training of Deep Bidirectional Transformers for Language Understanding," CoRR, Submitted on Oct. 11, 2018, arXiv:1810.04805v1, 14 pages.

Diez et al., "iCodon customizes gene expression based on the codon composition," Scientific Reports, Jul. 15, 2022, 12(1):12126.

Ding et al., "MPEPE, a predictive approach to improve protein expression in E. coli based on deep learning," Computational and Structural Biotechnology Journal, Jan. 1, 2022, 20:1142-1153.

Groher et al., "Riboswitching with ciprofloxacin-development and characterization of a novel RNA regulator," Nucleic Acids Research, Feb. 28, 2018, 46(4):2121-2132.

Groher et al., "Tuning the performance of synthetic riboswitches using machine learning," ACS Synthetic Biology, Jan. 18, 2019, 8(1):34-44.

Jackson et al., "An mRNA vaccine against SARS-CoV-2—preliminary report," New England Journal of Medicine, Nov. 12, 2020, 383(20):1920-1931.

Jackson et al., "The promise of mRNA vaccines: a biotech and industrial perspective," NPJ Vaccines, Feb. 4, 2020, 5(1):11.

Ji et al., "DNABERT: pre-trained Bidirectional Encoder Representations from Transformers model for DNA-language in genome," Bioinformatics, Aug. 1, 2021, 37(15):2112-20.

Leppek et al., "Combinatorial optimization of mRNA structure, stability, and translation for RNA-based therapeutics," Nature Communications, Mar. 22, 2022, 13(1):1536.

Li et al., "Codonbert: Large language models for mRNA design and optimization," bioRxiv, Sep. 12, 2023, 19 pages.

Li et al., "LinearTurboFold: linear-time global prediction of conserved structures for RNA homologs with applications to SARS-CoV-2," Proceedings of the National Academy of Sciences, Dec. 28, 2021, 118(52):e2116269118.

Lorentzen et al., "Clinical advances and ongoing trials of mRNA vaccines for cancer treatment," The Lancet Oncology, Oct. 1, 2022, 23(10):e450-458.

Manato et al., "Informative RNA base embedding for RNA structural alignment and clustering by deep representation learning," NAR Genomics and Bioinformatics, Feb. 22, 2022, 4(1):lqac012.

Maruggi et al., "Immunogenicity and protective efficacy induced by self-amplifying mRNA vaccines encoding bacterial antigens," Vaccine, Jan. 5, 2017, 35(2):361-368.

Mauger et al., "mRNA structure regulates protein expression through changes in functional half-life," Proceedings of the National Academy of Sciences, Nov. 26, 2019, 116(48):24075-24083.

Mauro et al., "A critical analysis of codon optimization in human therapeutics," Trends in Molecular Medicine, Nov. 1, 2014, 20(11):604-613.

Mauro, "Codon optimization in the production of recombinant biotherapeutics: potential risks and considerations," BioDrugs, Feb. 2018, 32(1):69-81.

McInnes et al., "Umap: Uniform Manifold Approximation and Projection for Dimension Reduction," CoRR, Submitted on Sep. 18, 2020, arXiv:1802.03426v3, 63 pages.

Miao et al., "mRNA vaccine for cancer immunotherapy," Molecular Cancer, Feb. 25, 2021, 20(1):41.

Mikolov et al., "Efficient Estimation of Word Representations in Vector Space," CoRR, Submitted on Jan. 16, 2013, arXiv:1301.3781, 9 pages.

Nieuwkoop et al., "Revealing determinants of translation efficiency via whole-gene codon randomization and machine learning," Nucleic Acids Research, Mar. 21, 2023, 51(5):2363-2376.

Pardi et al., "mRNA vaccines—a new era in vaccinology," Nature Reviews Drug Discovery, Jan. 12, 2018, 17(4):261-279.

Pardi et al., "Recent advances in mRNA vaccine technology," Current Opinion in Immunology, Aug. 1, 2020, 65:14-20.

Pardi et al., "Zika virus protection by a single low-dose nucleoside-modified mRNA vaccination," Nature, Mar. 9, 2017, 543(7644):248-251.

Parret et al., "Critical reflections on synthetic gene design for recombinant protein expression," Current Opinion in Structural Biology, Jun. 1, 2016, 38:155-162.

Peters et al., "Deep Contextualized Word Representations," North American Chapter of the Association for Computational Linguistics, Jun. 1, 2018, pp. 2227-2237.

Pilkington et al., "From influenza to COVID-19: Lipid nanoparticle mRNA vaccines at the frontiers of infectious diseases," Acta Biomaterialia, Sep. 1, 2021, 131:16-40.

Radford et al., "Improving language understanding by generative pre-training," 2018, 12 pages.

Rajaraman et al., "Mining of Massive Datasets," Cambridge University Press, Nov. 23, 2011, 513 pages.

(56) References Cited

OTHER PUBLICATIONS

Rives et al., "Biological structure and function emerge from scaling unsupervised learning to 250 million protein sequences," Proceedings of the National Academy of Sciences, Apr. 5, 2021, 118(15):e2016239118.

Schlake et al., "Developing mRNA-vaccine technologies," RNA Biology, Nov. 1, 2012, 9(11):1319-1330.

Schmidt et al., "SICOR: Subgraph isomorphism comparison of rna secondary structures," IEEE/ACM Transactions on Computational Biology and Bioinformatics, Jul. 10, 2019, 17(6):2189-2195.

Shen et al., "E2Efold-3D: End-to-End Deep Learning Method for accurate de novo RNA 3D Structure Prediction," CoRR, Submitted on Jul. 4, 2022, arXiv:2207.01586v1, 17 pages.

Vaswani et al., "Attention Is All You Need," Advances in Neural Information Processing Systems, Dec. 4, 2017, 30:1-11.

Wayment-Steele et al., "Deep learning models for predicting RNA degradation via dual crowdsourcing," Nature Machine Intelligence, Dec. 14, 2022, 4(12):1174-1184.

Webster et al., "Synthetic gene design—The rationale for codon optimization and implications for molecular pharming in plants," Biotechnology and Bioengineering, Mar. 2017, 114(3):492-502.

Wheeler et al., "Database resources of the national center for biotechnology information," Nucleic Acids Research, Nov. 27, 2007, 36(suppl_1):D13-D21.

Wint et al., "Kingdom-wide analysis of fungal protein-coding and tRNA genes reveals conserved patterns of adaptive evolution," Molecular Biology and Evolution, Feb. 1, 2022, 39(2):msab372.

Zhang et al., "A Sensitivity Analysis of (and Practitioners' Guide to) Convolutional Neural Networks for Sentence Classification," CoRR, Submitted on Oct. 13, 2015, arXiv:1510.03820v1, 18 pages.

Zhang et al., "Advances in mRNA vaccines for infectious diseases," Frontiers in Immunology, Mar. 27, 2019, 10:594.

Zhang et al., "Algorithm for optimized mRNA design improves stability and immunogenicity," Nature, May 2, 2023, 621(7978):396-403.

* cited by examiner

| Dataset | mRNA half-life | Translation rate | Transcript expression | Protein expression |
|---|---|---|---|---|
| Data size | 12971 | 8428 | 4401 | 7135 |
| Metric | Spearman ↑ | | | AUROC ↑ |
| RNA-FM | 0.524 | 0.455 | 0.256 | 0.614 |
| Saluki | 0.558 | 0.598 | 0.335 | 0.564 |
| mRNA-LM | 0.642 | 0.626 | 0.384 | 0.652 |

FIG. 7

PREDICTING mRNA PROPERTIES USING LARGE LANGUAGE TRANSFORMER MODELS

CROSS-REFERENCE TO RELATED APPLICATION

This application claims priority to U.S. Provisional Patent Application No. 63/516,226, filed on Jul. 28, 2023, U.S. Provisional Patent Application No. 63/648,338, filed on May 16, 2024, and European Patent Application EP24305758.5, filed on May 16, 2024, the disclosures of all of which are hereby incorporated by reference in their entirety.

TECHNICAL FIELD

This specification generally relates to predicting properties of mRNA molecules using machine-learning models, such as large language transformer models.

BACKGROUND

The mRNA, or messenger RNA, is a type of RNA molecule that plays a crucial role in gene expression and protein synthesis. The primary function of mRNA is to carry the genetic instructions from DNA to the ribosomes, where proteins are synthesized. mRNA is typically single-stranded and can be several hundred to several thousand nucleotides in length. A full-length mRNA sequence includes a 5' untranslated region (UTR), a coding sequence (CDS), and a 3' UTR. The 5' UTR is a non-coding sequence at the beginning of the mRNA molecule. The 3' UTR is a non-coding sequence located at the end of the mRNA molecule. The CDS consists of a sequence of codons, where each codon consists of three nucleotides that specify a particular amino acid or a start or a stop signal during protein synthesis. The sequence of codons determines the order in which amino acids are assembled during translation. Although the 5' and 3' UTRs are not translated, they can play an important role in mRNA stability, localization, and translation regulation.

A machine-learning model is a computational model that learns patterns and relationships in data, and then uses that knowledge to represent the data in a different space and make predictions or decisions on new data. Neural networks are machine learning models that employ one or more layers of nonlinear units to predict an output for a received input. The output of each hidden layer is used as input to the next layer in the network, i.e., the next hidden layer or the output layer. Each layer of the network generates an output from a received input in accordance with current values of a respective set of parameters.

SUMMARY

This disclosure describes methods, computer systems, and apparatus, including computer programs encoded on computer storage media, for predicting properties of mRNA molecules.

In one aspect, this disclosure provides a prediction method for predicting one or more properties of an mRNA molecule. The method can be implemented by a system including one or more computers. In general, the system generates token representations by numerically encoding the codon sequences of mRNA sequences, uses unsupervised learning to generate embedded features of the mRNA sequences using an embedding machine-learning model (such as a large language model), and further uses supervised learning to predict mRNA properties for downstream tasks. By pre-training a large language model, the system enables the model to generate high-performance embeddings that capture meaningful representations, codon interactions, and sequence-level patterns essential for understanding and predicting various mRNA properties in downstream tasks. The down-stream tasks can include, for example, (1) predicting mRNA expressions, (2) analyzing mRNA stability, and (3) predicting mRNA degradation. The two-step process including the pre-training and downstream task-based fine-tuning make it possible to generate high-quality predictions of the mRNA properties based on limited labeled data.

To perform the prediction method, the system obtains data representing a codon sequence of the mRNA molecule, generates an input token vector by numerically encoding the codon sequence, and generates an embedded feature vector by processing the input token vector using an embedding machine-learning model having a first set of model parameters. The first set of model parameters have been updated using a first training process of a first machine-learning model that includes the embedding machine-learning model. The first training process is performed based on a dataset specifying known codon sequences of mRNA molecules, and the first machine-learning model is configured to perform one or more pre-training tasks. The system processes the embedded feature vector using a property-prediction machine-learning model to generate an output that predicts one or more properties of the mRNA molecule. The property-prediction machine-learning model has a second set of model parameters that have been updated using a second training process, based on a plurality of training examples, of a second machine-learning model including the property-prediction machine-learning model. Each respective training example includes (i) a respective training input specifying a representation of a respective mRNA molecule and (ii) a respective label specifying one or more properties of the respective mRNA molecule.

In some implementations of the prediction method, the pre-training tasks include a masked language model (MLM) learning task for predicting masked codons within a known mRNA molecule. In these cases, the loss function can include an MLM loss function defined as $\mathcal{L}_{MLM} = \mathbb{E}_{x \sim X} \mathbb{E}_M \Sigma_{i \in M} -\log\, p(x_i | x_M)$, where X represents a batch of sequences, $p(x_i | x_M)$ represents a probability of the first machine-learning model predicting that a token $x_i$ is present at a particular masked position i, given an unmasked portion $x_M$ of an input sequence x.

In some cases, the pre-training tasks includes a homology sequence prediction (HSP) task for predicting whether two input mRNA sequences belong to organisms in a same homology class. In these cases, the loss function can include an HSP loss function defined as: $\mathcal{L}_{HSP} = -\mathbb{E}_N \Sigma_{n=1}^{N} [y_n \log p_n + (1-y_n)\log(1-p_n)]$, where $y_n$ represents a ground truth label of whether two input token sequences represent mRNA codon sequences belonging to a same homology class, and $p_n$ represents a predicted probability that the two input token sequences represent mRNA codon sequences belonging to the same homology class.

In some cases, the loss function combines an MLM loss and an HSP loss.

In some implementations of the prediction method, the one or more properties of the mRNA molecule includes an expression level of the mRNA molecule in a specific type of cell or tissue. For example, the mRNA molecule can be a component of a vaccine and is encoded for expressing one or more antigenic proteins of a target pathogen, and the predicted properties of the mRNA molecule can characterize expression levels of the antigenic proteins of the target pathogen in the specific type of cell or tissue.

In some implementations of the prediction method, the one or more properties of the mRNA molecule includes a stability under one or more environmental conditions.

In some implementations of the prediction method, the one or more properties of the mRNA molecule includes a switching factor of the mRNA molecule in a specific type of cell or tissue.

In some implementations of the prediction method, the one or more properties of the mRNA molecule includes a degradation rate of the mRNA molecule under one or more environmental conditions. For example, the mRNA molecule can be a component of a SARS-CoV-2 vaccine, and the property-prediction machine-learning model can predict the degradation rate of the mRNA molecule under a physiological condition.

In some implementations of the prediction method, generating the input token vector includes mapping each codon of the codon sequence to a respective numerical value, and generating the token vector by concatenating the numerical values.

In some implementations of the prediction method, the first machine-learning model includes a large language model (LLM).

In some implementations of the prediction method, the first machine-learning model includes a bidirectional transformer.

In some implementations of the prediction method, the property-prediction machine-learning model includes one or more of: a neural network, a K-nearest neighbors model, a support vector machine, a decision trees model, a random forest model, or a ridge regression model.

In some implementations of the prediction method, the property-prediction machine-learning model includes a convolutional neural network (CNN).

In another aspect, this disclosure provides another prediction method for predicting one or more properties of an mRNA molecule. The method can be implemented by a system including one or more computers. The system obtains data representing an mRNA molecule, the mRNA molecule including (i) a 5' untranslated region (UTR), (ii) a coding sequence (CDS), and (iii) a 3' UTR. The system generates a first input token vector by numerically encoding a nucleotide sequence of the 5' UTR of the mRNA molecule, generates a second input token vector by numerically encoding a codon sequence of the CDS of the mRNA molecule, and generates a third input token vector by numerically encoding a nucleotide sequence of the 3' UTR of the mRNA molecule.

The system generates a first embedded feature vector by processing the first input token vector using a first embedding machine-learning model, generates a second embedded feature vector by processing the second input token vector using a second embedding machine-learning model, and generates a third embedded feature vector by processing the third input token vector using a third embedding machine-learning model. The first, the second, and the third embedding machine-learning models have been trained on a set of training mRNA sequences using a first training process. In some cases, the first, the second, and the third embedding machine-learning models were separately trained in the first training process. In some cases, the first, the second, and the third embedding machine-learning models were jointly trained in the first training process.

The system generates a joint embedding by combining the first embedded feature vector, the second embedded feature vector, and the third embedded feature vector. The system processes the joint embedding using a property-prediction machine-learning model to generate an output that predicts one or more properties of the mRNA molecule. The property-prediction machine-learning model has been trained on a set of labeled training examples using a second training process.

In some implementations of the prediction method, to generate the first input token vector, the system maps each nucleotide of the nucleotide sequence of the 5' UTR to a respective numerical value, and generates the first input token vector by concatenating the numerical values. To generate the second input token vector, the system maps each codon of the codon sequence of the CDS to a respective numerical value, and generates the second input token vector by concatenating the numerical values. To generate the third input token vector, the system maps each nucleotide of the nucleotide sequence of the 3' UTR to a respective numerical value, and generates the third input token vector by concatenating the numerical values.

In some implementations of the prediction method, to generate the joint embedding, the system performs a first pooling operation on the first embedded feature vector to generate a first embedding, performs a second pooling operation on the second embedded feature vector to generate a second embedding, performs a third pooling operation on the third embedded feature vector to generate a third embedding; and concatenates the first embedding, the second embedding, and the third embedding to generate the joint embedding.

In some implementations of the prediction method, each of the first, the second, and the third pooling operations is a mean pooling operation.

In some implementations of the prediction method, the first training process includes: initiating values of parameters of a first machine-learning model including the first, the second, and the third embedding machine-learning models, and training the first machine-learning model by minimizing a pre-training loss function including one or more pre-training losses defined for one or more pre-training tasks. In some cases, the one or more pre-training tasks include a masked language model (MLM) learning task for predicting one or more masked codons or nucleotides within a known mRNA molecule. In some cases, the one or more pre-training losses include an MLM loss function defined as: $\mathcal{L}_{MLM} = \mathbb{E}_{x \sim X} \mathbb{E}_M \Sigma_{i \in M} -\log p(x_i|x_M)$, where X represents a batch of sequences, $p(x\_i|x\_M)$ represents a probability of the first machine-learning model predicting that a token $x_i$ is present at a particular masked position i, given an unmasked portion $x_M$ of an input sequence x. In some cases, one or more pre-training tasks include a homology sequence prediction (HSP) task for predicting whether two training mRNA sequences belong to organisms in a same homology class. In some cases, the one or more pre-training losses include an HSP loss function defined as: $\mathcal{L}_{HSP} = -\mathbb{E}_N \Sigma_{n=1}^{N} [y_n \log p_n + (1-y_n)\log(1-p_n)]$, where $y_n$ represents a ground truth label of whether two input token sequences represent mRNA codon sequences belonging to a same homology class, and $p_n$ represents a predicted probability that the two input token sequences represent mRNA codon sequences belonging to the same homology class. In some cases, the pre-training loss function combines an MLM loss and an HSP loss.

In some implementations of the prediction method, the second training process includes: initiating values of parameters of a second machine-learning model including the property-prediction machine-learning model; and training the second machine-learning model by minimizing a downstream loss function including one or more prediction losses defined for one or more property prediction tasks.

In some implementations of the prediction method, the pre-training loss function or the downstream loss function further includes a contrastive loss that aims to maximize similarities between embeddings of different regions within a same mRNA sequence while minimizing the similarities between the embeddings of different regions from different mRNA sequences.

In some cases, the contrastive loss includes a first contrastive loss that aims to maximize the similarity between the embeddings of the 5' UTR and the CDS within the same mRNA sequence while minimizing the similarity between the embeddings of the 5' UTR and the CDS from two different mRNA sequences.

In some cases, the first contrastive loss is computed by $$\mathcal{L}_{C1} = -\frac{1}{N}\sum_{i=1}^{N} \log \frac{\exp\left(sim\left(u_i, v_i\right)/\tau\right)}{\sum_{j=1}^{N}\exp\left(sim\left(u_i, v_j\right)/\tau\right)},$$

where N is the batch size of a batch of training examples, u and v are normalized embeddings generated for a 5' UTR and a CDS, respectfully, sim(.,.) is the cosine similarity, and i is a temperature parameter.

In some cases, the contrastive loss includes a second contrastive loss that aims to maximize the similarity between the embeddings of the 3' UTR and the CDS within the same mRNA sequence while minimizing the similarity between the embeddings of the 3' UTR and the CDS from two different mRNA sequences.

In some cases, the contrastive loss is computed as a combined contrastive loss that combines the first contrastive loss and the second contrastive loss. For example, the combined contrastive loss can be computed as an average of the first contrastive loss and the second contrastive loss.

In some implementations of the prediction method, the one or more properties of the mRNA molecule includes an expression level of the mRNA molecule in a specific type of cell or tissue.

In some cases, the mRNA molecule is a component of a vaccine and is encoded for expressing one or more antigenic proteins of a target pathogen, and the predicted properties of the mRNA molecule characterize expression levels of the antigenic proteins of the target pathogen in the specific type of cell or tissue.

In some implementations of the prediction method, the one or more properties of the mRNA molecule includes a stability under one or more environmental conditions.

In some implementations of the prediction method, the one or more properties of the mRNA molecule includes a switching factor of the mRNA molecule in a specific type of cell or tissue.

In some implementations of the prediction method, the one or more properties of the mRNA molecule includes a degradation rate of the mRNA molecule under one or more environmental conditions.

In some cases, the mRNA molecule is a component of a SARS-CoV-2 vaccine, and the property-prediction machine-learning model is configured to predict the degradation rate of the mRNA molecule under a physiological condition.

In some implementations of the prediction method, each of the first, the second, and the third embedding machine-learning models includes a respective large language model (LLM).

In some implementations of the prediction method, each of the first, the second, and the third embedding machine-learning models includes a respective bidirectional transformer.

In some implementations of the prediction method, the property-prediction machine-learning model includes one or more of: a neural network, a K-nearest neighbors model, a support vector machine, a decision trees model, a random forest model, or a ridge regression model.

In some implementations of the prediction method, the property-prediction machine-learning model includes a convolutional neural network (CNN).

In another aspect, this disclosure provides a design method for determining the optimal codon sequence of an mRNA for performing a particular task. The design method can be implemented by a system including one or more computers. The system predicts properties of each of the candidate mRNA molecules using one of the prediction methods described above, and selects the mRNA molecule from the set of candidate mRNA molecules based on the predicted properties. In some cases, the design method further includes physically generating the selected mRNA molecule.

In some implementations of the design method, the downstream task includes one or more of: maximizing an expression level of the mRNA in a specific type of cell or tissue or maximizing a stability of the mRNA in a specific environment.

In another aspect, this disclosure provides the mRNA molecule selected using the design method.

In another aspect, this disclosure provides a reinforcement-learning (RL) method for training an RL model for determining the optimal codon sequence of an mRNA for performing a particular task. The RL method can be implemented by a system including one or more computers. The system maintains data representing a set of candidate sequences for the mRNA molecule, and uses a reinforcement-learning (RL) model to process one or more of the candidate sequences to generate one or more new sequences. The RL model has been trained using a reward signal including mRNA molecule properties predicted using one of the prediction methods described above. The system selects an optimal sequence from the new sequences. In some cases, the RL method further includes physically generating an mRNA molecule having the optimal sequence selected from the new sequences.

In another aspect, this disclosure provides the mRNA molecule having the optimal sequence selected from the new sequences generated using the RL method.

In another aspect, this disclosure provides a training method for training a prediction model for predicting properties of mRNA molecules. The training method can be implemented by a system including one or more computers. The prediction model includes (i) an embedding machine-learning model configured to generate an embedded feature vector for a model input representing a codon sequence of the mRNA molecule and (ii) a property-prediction machine-learning model configured to process the embedded feature vector to generate an output specifying one or more properties of the mRNA molecule. The system obtains a first dataset including a set of sequence representations of mRNA molecules, and trains a first machine-learning model including the embedding machine-learning model on one or more pre-training tasks using the first data set. The system obtains a second dataset including a plurality of training examples. Each respective training example includes (i) a respective training input specifying a representation of a respective mRNA molecule and (ii) a respective label characterizing one or more properties of the respective mRNA molecule. The system performs supervised learning of a second machine-learning model including the property-prediction machine-learning model on the second dataset.

In some implementations of the training method, the pre-training tasks include a masked language model (MLM) learning task for predicting masked codons within a known mRNA molecule. In these cases, the loss function can include an MLM loss function defined as $\mathcal{L}_{MLM} = \mathbb{E}_{x \sim X} \mathbb{E}_M \Sigma_{i \in M} -\log\ p(x_i | x_M)$, where X represents a batch of sequences, $p(x_i | x_M)$ represents a probability of the first machine-learning model predicting that a token $x_i$ is present at a particular masked position i, given an unmasked portion $x_M$ of an input sequence x.

In some implementations of the training method, the pre-training tasks includes a homology sequence prediction (HSP) task for predicting whether two input mRNA sequences belong to organisms in a same homology class. In these cases, the loss function can include an HSP loss function defined as:

$\mathcal{L}_{HSP} = -\mathbb{E}_N \Sigma_{n=1}^{N} [y_n \log\ p + (1-y_n)\log(1-p_n)]$, where $y_n$ represents a ground truth label of whether two input token sequences represent mRNA codon sequences belonging to a same homology class, and $p_n$ represents a predicted probability that the two input token sequences represent mRNA codon sequences belonging to the same homology class.

In some implementations of the training method, the loss function combines an MLM loss and an HSP loss.

In some implementations of the training method, the one or more properties of the mRNA molecule includes one or more of: an expression level of the mRNA molecule in a specific type of cell or tissue, a stability under one or more environmental conditions, or a switching factor of the mRNA molecule in a specific type of cell or tissue.

In some implementations of the training method, generating the input token vector includes mapping each codon of the codon sequence to a respective numerical value, and generating the token vector by concatenating the numerical values.

In some implementations of the training method, the first machine-learning model includes a large language model (LLM). For example, the first machine-learning can include a bidirectional transformer.

In some implementations of the training method, the property-prediction machine-learning model includes one or more of: a neural network, a K-nearest neighbors model, a support vector machine, a decision trees model, a random forest model, or a ridge regression model.

In another aspect, this disclosure provides a training method for training a prediction model for predicting properties of mRNA molecules. The training method can be implemented by a system including one or more computers. The mRNA molecule includes (i) a 5' untranslated region (UTR), (ii) a coding sequence (CDS), and (iii) a 3' UTR. The prediction model includes (i) a first embedding machine-learning model configured to process a first input token vector representing a nucleotide sequence of the 5' UTR of the mRNA molecule to generate a first embedded feature vector, (ii) a second embedding machine-learning model configured to process a second input token vector representing a codon sequence of the mRNA molecule to generate a second embedded feature vector, (iii) a third embedding machine-learning model configured to process a third input token vector representing a nucleotide sequence of the 3' UTR of the mRNA molecule to generate a third embedded feature vector, and (iv) a property-prediction machine-learning model configured to process a joint embedding generated by combining the first, the second, and the third embedded feature vector to generate an output specifying one or more properties of the mRNA molecule.

The system obtains a first dataset including a set of sequence representations of mRNA molecules. The system performs a first training process to train the first, the second, and the third embedding machine-learning models on one or more pre-training tasks using the first data set. The system obtains a second dataset including a plurality of training examples. Each respective training example includes (i) a respective training input specifying a representation of a respective mRNA molecule and (ii) a respective label characterizing one or more properties of the respective mRNA molecule. The system performs a second training process to train the property-prediction machine-learning model on one or more property prediction tasks using the second dataset. In some cases, the first, the second, and the third embedding machine-learning models are separately trained in the first training process. In some cases, the first, the second, and the third embedding machine-learning models are jointly trained in the first training process.

In some implementations of the training method, the first training process includes: initiating values of parameters of a first machine-learning model including the first, the second, and the third embedding machine-learning models; and training the first machine-learning model by minimizing a pre-training loss function including one or more pre-training losses defined for one or more pre-training tasks.

In some implementations of the training method, the one or more pre-training tasks include a masked language model (MLM) learning task for predicting masked codons within a known mRNA molecule.

In some implementations of the training method the pre-training loss function includes an MLM loss function defined as: $\mathcal{L}_{MLM} = \mathbb{E}_{x \sim X} \mathbb{E}_M \Sigma_{i \in M} -\log\ p(x_i | x_M)$, where X represents a batch of sequences, $p(x\_i | x\_M)$ represents a probability of the first machine-learning model predicting that a token $x_i$ is present at a particular masked position i, given an unmasked portion $x_M$ of an input sequence x.

In some implementations of the training method, the one or more pre-training tasks include a homology sequence prediction (HSP) task for predicting whether two input mRNA sequences belong to organisms in a same homology class.

In some cases, the pre-training loss function includes an HSP loss function defined as: $\mathcal{L}_{HSP} = -\mathbb{E}_N \Sigma_{n=1}^{N} [y_n \log\ p_n + (1-y_n)\log(1-p_n)]$, where $y_n$ represents a ground truth label of whether two input token sequences represent mRNA codon sequences belonging to a same homology class, and $p_n$ represents a predicted probability that the two input token sequences represent mRNA codon sequences belonging to the same homology class.

In some implementations of the training method, the pre-training loss function combines an MLM loss and an HSP loss.

In some implementations of the training method, the second training process includes: initiating values of parameters of a second machine-learning model including the property-prediction machine-learning model; and training the second machine-learning model by minimizing a downstream loss function including one or more prediction losses defined for one or more property prediction tasks.

In some cases, the pre-training loss function or the downstream loss function further includes a contrastive loss that aims to maximize similarities between embeddings of different regions within a same mRNA sequence while minimizing the similarities between the embeddings of different regions from different mRNA sequences.

In some cases, the contrastive loss includes a first contrastive loss that aims to maximize the similarity between the embeddings of the 5' UTR and the CDS within the same mRNA sequence while minimizing the similarity between the embeddings of the 5' UTR and the CDS from two different mRNA sequences.

In some cases, the first contrastive loss is computed by $$\mathcal{L}_{C1} = -\frac{1}{N}\sum_{i=1}^{N} \log \frac{\exp\left(sim\left(u_i, v_i\right)/\tau\right)}{\sum_{j=1}^{N} \exp\left(sim\left(u_i, v_j\right)/\tau\right)},$$

where N is the batch size of a batch of training examples, u and v are normalized embeddings generated for a 5' UTR and a CDS, respectfully, sim(.,.) is the cosine similarity, and i is a temperature parameter.

In some cases, the contrastive loss includes a second contrastive loss that aims to maximize the similarity between the embeddings of the 3' UTR and the CDS within the same mRNA sequence while minimizing the similarity between the embeddings of the 3' UTR and the CDS from two different mRNA sequences.

In some cases, the contrastive loss is computed as a combined contrastive loss that combines the first contrastive loss and the second contrastive loss.

In some cases, the combined contrastive loss is computed as an average of the first contrastive loss and the second contrastive loss.

In some cases, the contrastive loss is included in the pre-training loss function.

In some cases, the contrastive loss is included in the downstream loss function.

In some implementations of the training method, the one or more properties of the mRNA molecule includes one or more of: an expression level of the mRNA molecule in a specific type of cell or tissue; a stability under one or more environmental conditions; or a switching factor of the mRNA molecule in a specific type of cell or tissue.

In some implementations of the training method, the first input token vector is generated by: mapping each nucleotide of the nucleotide sequence of the 5' UTR to a respective numerical value, and generating the first input token vector by concatenating the numerical values; the second input token vector is generated by: mapping each codon of the codon sequence of the CDS to a respective numerical value, and generating the second input token vector by concatenating the numerical values; and the third input token vector is generated by: mapping each nucleotide of the nucleotide sequence of the 3' UTR to a respective numerical value, and generating the third input token vector by concatenating the numerical values.

In some implementations of the training method, each of the first, the second, and the third embedding machine-learning models includes a respective large language model (LLM).

In some implementations of the training method, each of the first, the second, and the third embedding machine-learning models includes a respective bidirectional transformer.

In some implementations of the training method, the property-prediction machine-learning model includes one or more of: a neural network, a K-nearest neighbors model, a support vector machine, a decision trees model, a random forest model, or a ridge regression model.

In some cases, the second machine-learning model further includes the first, the second, and the third embedding machine-learning models; initiating the values of parameters of the second machine-learning model includes initiating the parameters of the first, the second, and the third embedding machine-learning models to values obtained through the first training process; and the second training process includes (i) inserting one or more layers into each of the first, the second, and the third embedding machine-learning models, and (2) updating parameter values of the inserted layers while fixing the parameter values of the other layers of the first, the second, and the third embedding machine-learning models.

This disclosure also provides a system including one or more computers and one or more storage devices storing instructions that, when executed by the one or more computers, cause the one or more computers to perform the prediction method, the training method, the design method, or the RL method described above.

This disclosure also provides one or more computer storage media storing instructions that when executed by one or more computers, cause the one or more computers to perform the prediction method, the training method, the design method, or the RL method described above.

The subject matter described in this disclosure can be implemented in particular embodiments so as to realize one or more advantages.

The study of mRNA has gained significant importance in various fields, including molecular biology, genetics, and therapeutics. Understanding and predicting mRNA properties, such as expression level, stability, structure, and switching factors in particular tissues or cells, provides insights into gene expression, protein synthesis, and the development of mRNA-based therapies, such as mRNA vaccines and gene therapies.

Existing techniques for predicting mRNA properties typically do not take into account the position and order information of codons and long-range interactions between codons. These limitations result in limited prediction efficiency and accuracy.

This disclosure presents techniques that utilize deep learning and transformer models for computationally predicting mRNA properties based on the codon sequence of the mRNA. Compared to models that process RNA base sequence representations, the codon sequence representation of mRNA offers essential functional insights into the mRNA molecules, including the genetic code, translation process, start and stop signals, reading frame, and the resulting amino acid sequence. Utilizing language models to process codon sequence representations provides meaningful embedded features, enabling a deeper understanding of the genetic information and evolutionary relationships associated with mRNA molecules.

In particular, certain implementations of described techniques use a pre-training process, based on a large number of known mRNA sequences, to train a language model to perform two tasks: (i) a masked language model (MLM) learning task and (ii) a homology sequence prediction (HSP) task.

During the MLM learning task training, the language model is optimized to predict the masked codons within a known mRNA molecule by considering the interactions between the masked and unmasked codons, utilizing the remaining codons as context. Consequently, the MLM is capable of acquiring knowledge about codon representations, inter-codon interactions, and the relationships between codons and mRNA sequences.

The HSP task leverages the observation that mRNAs from organisms sharing a common evolutionary origin exhibit more pronounced similarities in their codon sequences. Therefore, training for the HSP task provides additional information and patterns regarding sequence-level representations for the mRNAs.

By pre-training the language model to perform both the MLM and HSP, the pre-training process enables the model to generate high-performance embeddings that capture meaningful representations, codon interactions, and sequence-level patterns essential for understanding and predicting various mRNA properties in downstream tasks. The two-step process including the pre-training and downstream task based fine-tuning make it possible to generate high-quality predictions of the mRNA properties based on limited labeled data.

Based on the predicted mRNA properties, the described system or another related system can determine optimal mRNA molecules for specific applications. For example, such a system can generate an output that indicates whether a particular mRNA is suitable for a particular application or an output that specifies the optimal mRNA molecule for the particular application. The system can transmit the output to a fabrication apparatus operative to implement the instruction to produce the mRNA. Overall, by training high-performance prediction models based on limited experimental data and using the trained model to predict mRNA properties, the described techniques can greatly improve the efficacy and efficiency of mRNA engineering.

In addition, in some implementations of the described techniques, the system uses two additional language models to generate embeddings of the nucleotide sequences of the 3' and 5' UTRs, and combines the embeddings generated for the CDS and the 3' and 5' UTRs as a combined embedding in pre-training. This approach allows the model to capture interactions and dependencies between coding and non-coding regions. As the 5' and 3' UTRs can play important roles in mRNA stability, localization, and translation regulation, combining their embeddings with the embedding generated from the codon sequence of the CDS enables the model to provide more accurate predictions for mRNA properties.

Furthermore, in some cases, the system incorporates a contrastive loss in the pre-training of the embedding models or the downstream training of the property prediction model, which enhances the model's ability to differentiate between similar and dissimilar mRNA sequences. The contrastive loss functions by minimizing the distance between embeddings generated for different regions within the same mRNA sequence while maximizing the distance between embeddings of different regions from different mRNA sequences. The contrastive loss helps the model to better capture the unique characteristics and interactions within an individual mRNA sequence, improving its ability to make accurate predictions about mRNA properties.

The above features enable the model to more effectively learn and generalize from the data, leading to higher accuracy and robustness in predicting mRNA stability, expression levels, and other properties. This enhancement is particularly valuable in applications requiring mRNA design, such as developing mRNA vaccines and gene therapies, where understanding the specific features of mRNA sequences is crucial for efficacy and safety. In addition, the improved performance of the model provides more efficient use of computational resources, such as reducing the time and cost associated with model training. For example, the model's enhanced learning capabilities allow it to achieve high performance with fewer tunings during training. As a result, the total computational load is decreased, which translates to lower energy consumption and shorter training periods.

The details of one or more embodiments of the subject matter described in this disclosure are set forth in the accompanying drawings and the description below. Other features, aspects, and advantages of the subject matter will become apparent from the description, the drawings, and the claims.

BRIEF DESCRIPTION OF THE DRAWINGS

FIG. 7 shows another performance comparison of different mRNA property prediction models for a variety of prediction tasks.

Like reference numbers and designations in the various drawings indicate like elements.

DETAILED DESCRIPTION

Predicting the properties of mRNA sequences is an important aspect of the development of mRNA-based therapeutics. For example, in mRNA, predicting mRNA stability, expression levels, and potential immunogenicity are crucial in designing effective mRNA agents, such as mRNA vaccines.

The expression level of an mRNA vaccine directly influences its potency and effectiveness. A higher expression level of the antigenic protein encoded within the mRNA leads to a stronger immune response. This also means a smaller dose of the vaccine can be effective, potentially making it simpler and more cost-efficient to manufacture. In addition, a high expression level helps overcome immune tolerance, a situation where the immune system becomes unresponsive to low levels of an antigen over time. Furthermore, it helps maintain the immune response for a longer duration, providing more lasting protection. The mRNA sequence is also crucial for its stability and function.

The traditional approach to identifying the optimal mRNA sequence is to choose codons based on their frequency in the target organism. However, relying solely on the most frequent codons has limitations and may not yield the best possible sequence.

Next-generation sequencing techniques have enabled researchers to generate thousands of mRNA sequences and measure their corresponding protein expression levels. However, the redundancy of the genetic code (64 codons for 21 amino acids) results in a vast search space that grows exponentially with sequence length. This makes it unfeasible to test all possible mRNA candidates experimentally.

Furthermore, in addition to the coding sequence (CDS), a full-length mRNA sequence further includes a 5' untranslated region (UTR) at the beginning of the mRNA molecule and a 3' UTR at the end of the mRNA molecule. Although the 5' and 3' UTRs are not translated, they have been shown to play an important role in mRNA stability, localization, and translation regulation. The impact of the 5' and 3' UTRs as well as their interactions with the CDS are not taken into account by conventional techniques.

Therefore, advanced computational models are needed to guide the search for optimal sequences.

Figure 1:
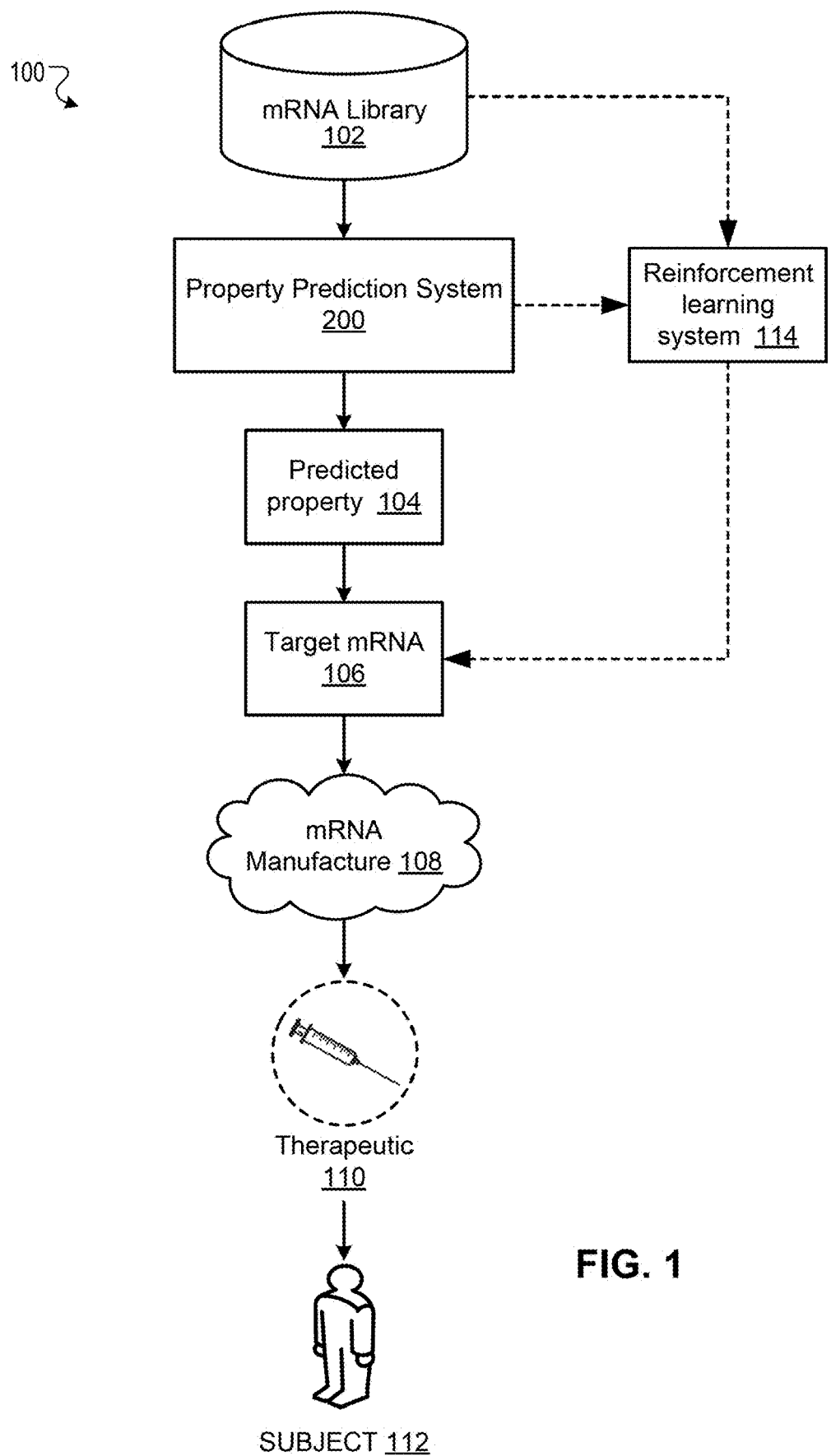
FIG. 1 shows an example workflow in an application scenario using a property prediction system to predict a property of an mRNA sequence.

FIG. 1 shows an example workflow 100 in an application scenario using a property prediction system 200 to predict a property of an mRNA sequence. In particular, FIG. 1 shows using the property prediction system 200 to select or design an mRNA sequence for a particular clinical application.

The mRNA library 102 defines a set of candidate mRNAs, where each mRNA can be represented by a respective codon sequence. In these implementations, the codon sequence represents coding sequence (CDS) of the candidate mRNA. In some other implementations. The representation for a candidate mRNA can include additional sequence information from the 3' and 5' untranslated regions (UTRs). When only the CDS is considered, the impacts of the UTRs on mRNA properties are not taken into account. For brevity, through this Specification, the term "mRNA codon sequence" refers to the codon sequence of the CDS of an mRNA molecule, while the term "mRNA sequence" may refer to either the full mRNA sequence (including the UTRs and the CDS) or solely the CDS codon sequence, depending on the specific context. The mRNA library 102 can include any appropriate number of mRNAs, e.g., 1 hundred, 1 thousand, 10 thousand, or 1 million mRNAs.

The property prediction system 200 is configured to process an mRNA codon sequence (e.g., from the mRNA library 102) to generate a property measure 104 for the mRNA that characterizes a predicted property of the corresponding mRNA in some implementations. In some other implementations, the property prediction system 200 is configured to process a full-length mRNA sequence (e.g., from the mRNA library 102) to generate the property measure 104 for the mRNA that characterizes a predicted property of the corresponding mRNA. The property measure 104 can include, for example, expression levels of one or more proteins (e.g., antigenic proteins of a target pathogen) of the mRNA in a specific type of cell or tissue, a stability under one or more environmental conditions, a switching factor of the mRNA molecule in a specific type of cell or tissue, or a degradation rate of the mRNA molecule under one or more environmental conditions.

The property prediction system 200 can screen the mRNA library 102 to identify mRNAs having desirable property measures. More specifically, the property prediction system 200 can predict a respective property measure 104 for each mRNA in the mRNA library 102. The property prediction system 200 can designate a proper subset of the mRNAs in the mRNA library 102 as being "target" mRNAs 106 based at least in part on the predicted property measures 104.

The property prediction system 200 can select a proper subset of the mRNAs in the mRNA library to be designated as target mRNAs in any variety of ways. For instance, the property prediction system 200 can designate any mRNA having a property measure 104 that satisfies a predefined threshold as being a target mRNA. As another example, the property prediction system 200 can designate a predefined number of mRNAs having the highest property measures 104 as being target mRNAs.

In some cases, the property prediction system 200 can be used with a reinforcement learning system 114 to determine the optimal codon sequence of an mRNA. In some cases, the property prediction system 200 can be used with a reinforcement learning system 114 to determine the optimal full sequence of an mRNA. The reinforcement learning system 114 uses a reinforcement-learning (RL) model to process one or more of the candidate sequences to generate one or more new sequences. The RL model can be trained using a reward signal including mRNA molecule properties predicted using the prediction system 200. An optimal sequence can be selected from the new sequences.

The generated or selected target mRNAs can be manufactured 108 using any suitable techniques and used in any variety of applications. For example, the manufactured mRNAs can be applied as a therapeutic 110 to a subject 112 to achieve a therapeutic effect in the subjects, such as an mRNA vaccine for an infectious disease or a cancer, or as a gene delivery agent to treat genetic disorders.

Figure 2A:
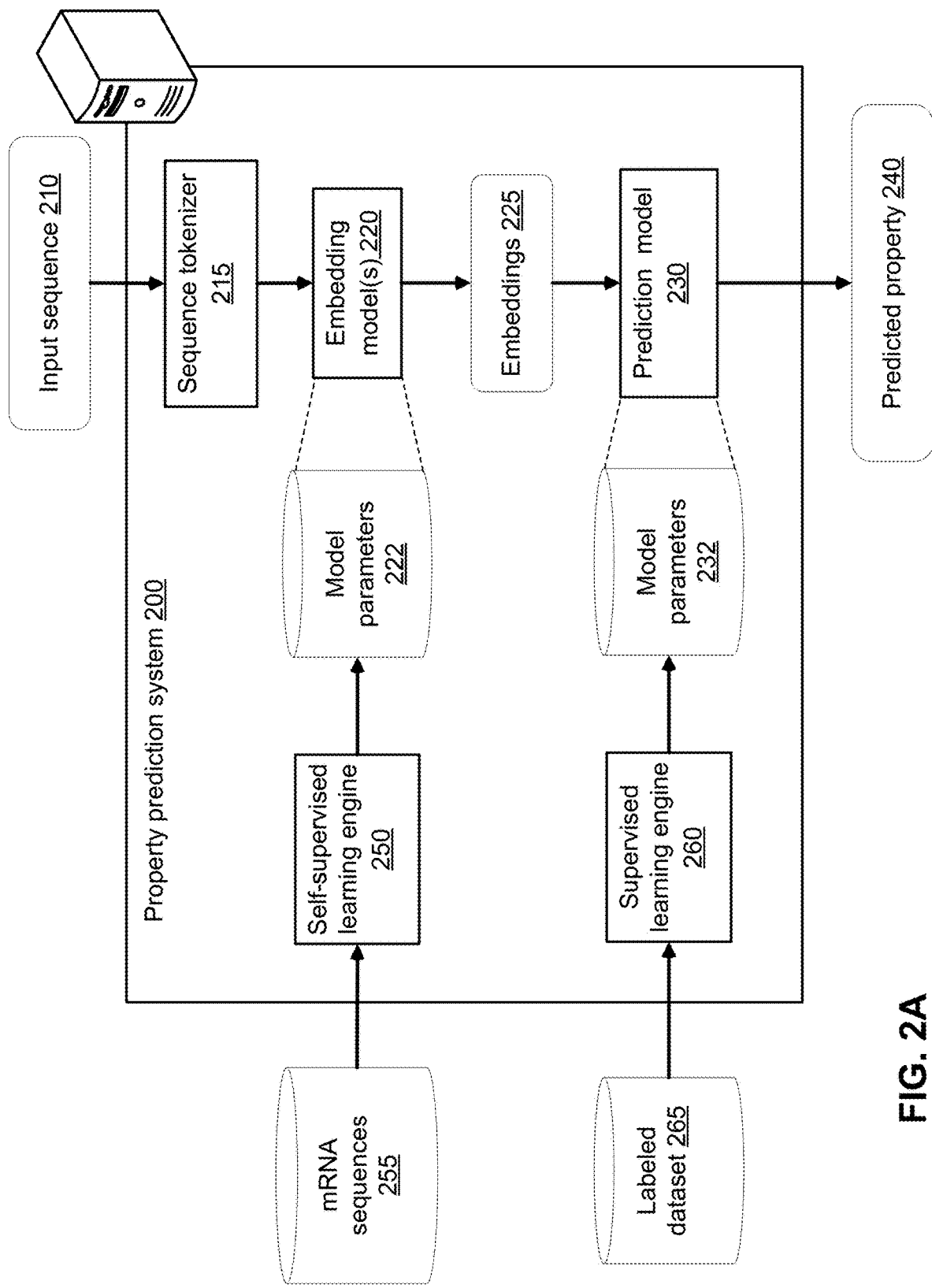
FIG. 2A shows an example of an mRNA property prediction system.

FIG. 2A shows an example of a property prediction system 200. The system 200 is an example of a system implemented as computer programs on one or more computers in one or more locations, in which the systems, components, and techniques described below can be implemented.

In general, the property prediction system 200 processes input data 210 specifying the codon sequence of an mRNA to predict the property measure 240 in some implementations. In some other implementations, the input data 210 specifies a full sequence of the mRNA. The property prediction system 200 includes a sequence tokenizer 215 that generates an input token vector by numerically encoding the codon sequence, an embedding machine-learning model 220 that processes the input token vector to generate an embedded feature vector 225, and a prediction machine-learning model 230 that processes the embedded feature vector 225 to generate an output that predicts one or more properties 240 of the mRNA molecule. In some cases, the sequence tokenizer 215 generates the input token vector by numerically encoding the full sequence mRNA sequence. The predicted properties can include one or more of: an expression level of the mRNA molecule in a specific type of cell or tissue, a stability under one or more environmental conditions, and/or a switching factor of the mRNA molecule in a specific type of cell or tissue.

In some implementations, the input mRNA sequence 210 is represented by the CDS codon sequence of the mRNA. The sequence tokenizer 215 can map each codon of a list of codons (e.g., a list of all 64 codons) to a respective numerical value. After mapping each codon of the input codon sequence 210 to the corresponding numerical number, the tokenizer 215 can generate the token vector for the input codon sequence 210 by concatenating the mapped numerical values.

In some other implementations, the input mRNA sequence 210 is the full mRNA sequence including the 5' and 3' UTRs as well as the CDS. The tokenization process in these cases will be described in further detail with reference to FIG. 2B.

The embedding machine-learning model 220 is configured to process the input token vector to generate an embedded feature vector 225. The embedded feature vector 225 is a numerical representation that captures the essential information required for one or more tasks. In particular, the embedded feature vector 225 can be a high-dimensional vector of real numbers that captures features of the mRNA codon sequence. In some cases, as will be described in further detail with reference to FIG. 2B, the embedding machine-learning model 220 can include multiple embedding models (e.g., 220a, 220b, and 220c with reference to FIG. 2B), and the embeddings 225 are joint embeddings computed by combining the embeddings generated by the multiple embedding models.

In some implementations, the embedding machine-learning model 220 is a neural network. The embedding neural network can adopt any appropriate architecture. In particular, the embedding neural network 220 can include at least a portion (e.g., the embedding portion) of a state-of-the-art large language model (LLM).

In some implementations, the embedding neural network 220 can include a bidirectional transformer, e.g., a bidirectional encoder representations from transformers (BERT) model. Implementation examples of the BERT are described in "BERT: Pre-training of Deep Bidirectional Transformers for Language Understanding," Devlin et al., arXiv: 1810.04805, 2018.

In an illustrative example of a particular implementation, the embedding neural network 220 includes a stack (e.g., 12 layers) of bidirectional transformer encoders. Each transformer layer processes its input by a set of (e.g., 12) self-attention heads, and outputs a representation for each position. In each layer, the multi-head self-attention mechanism captures the contextual information of the input sequence by considering all the other codons in the sequence. A key benefit of the self-attention mechanism is the connection learned between all pairs of positions in an input sequence using parallel computation enabling implementation to model not only short-range but also long-range interactions, which impact translation efficiency and stability. In some implementations, after the self-attention layers, the embedding neural network 220 further includes one or more feedforward layers that apply a non-linear transformation to the output hidden representation from the self-attention layers. A residual connection can be employed around each of the multi-head attention and feedforward layers. After processing the input sequence with a stack of transformer encoders, the embedding neural network 220 produces the final contextualized codon representations, which can be followed by a classification layer to produce probability distribution over the vocabulary during pre-training.

The prediction machine-learning model 230 is configured to process an input including the embedded feature vector 225 to generate an output 240 that predicts a property measure 240 of the mRNA. The prediction machine-learning model 230 can be any appropriate model, and can be implemented with one or more of a neural network, a K-nearest neighbors model, a support vector machine, a decision trees model, a random forest model, or a ridge regression model.

In some implementations, the system 200 or another system includes a self-supervised learning engine 250 configured to update the model parameters 222 of the embedding machine-learning model using self-supervised learning, based on a set of mRNA codon sequence representations 255. In some cases, the self-supervised learning engine 250 configured to update the model parameters 222 of multiple embedding machine-learning models 220 using self-supervised learning, based on a set of full-length mRNA sequence representations 255.

The goal of the self-supervised learning is to learn meaningful embeddings of mRNA codon sequences without needing to use labeled data. In particular, the self-supervised learning engine 250 learns the embeddings using unlabeled mRNA codon sequence data, that is, data specifying or representing each of a set of mRNA codon sequences without mRNA property labels. That is, the self-supervised learning engine 250 can leverage the large number of known mRNA codon sequences to learn the embeddings without needing to obtain a large amount of experimental benchmark data for the properties of the known mRNAs. In general, the dataset 225 includes a large number of mRNA codon sequences, e.g., hundreds of thousands of mRNA sequences, millions of mRNA sequences, tens of millions of mRNA sequences, or hundreds of millions of mRNA sequences.

In some cases, the goal of the self-supervised learning is to learn meaningful embeddings of full-length mRNA sequences without needing to use labeled data. In particular, the self-supervised learning engine 250 learns the embeddings using unlabeled full-length mRNA sequence data, that is, data specifying or representing each of a set of mRNA sequences without mRNA property labels.

The training dataset 225 can include mRNA codon sequences across multiple organisms, including, for example, mRNA sequences of mammalian origin, bacterial origin, yeast origin, and virus origin. In one particular example, reference mRNA sequences are obtained from the NCBI datasets, which include mammalian reference sequences, *Escherichia coli* (*E. coli*) reference sequences, and *Homo sapiens* virus complete nucleotides. In some cases, the reference sequences are pre-processed and filtered to exclude invalid and replicate sequences. For example, the pre-processing and filtering can include: requiring the mRNA sequence with the sequence length multiples of 3, replacing the nucleotide T with U, starting with the start codon ("AUG") and ending with stop codons ("UAA", "UAG", "UGA"), and/or only including nucleotides from the set {A, U, G, C, N}.

In some cases, mammalian sequences can be divided into three groups: marsupials, monotremes, and placentals. Placentals, containing the vast majority of extant mammals, can be further categorized into nine subgroups: primates, carnivores, rodents, even-toed ungulates, bats, odd-toed ungulates, insectivores, rabbits, and more placentals.

A codon has three adjacent nucleotides, and each position has five choices {A, U, G, C, N} after pre-processing. Therefore, there are $5^3$ (125) possibilities of combination. Additionally, in some cases, five special tokens are added to the vocabulary: classifier token [CLS], separator token [SEP], unknown token [UNK], padding token [PAD], and masking token [MASK]. In total, there are 130 tokens in the vocabulary of the embedding model 220.

The self-supervised learning engine 250 initiates values of parameters 222 of a first machine-learning model comprising the embedding model 220, and updates the values of the parameters by minimizing a loss function defined for one or more pre-training tasks. In some cases, the pre-training tasks can include a masked language model (MLM) learning task for predicting masked codons within a known mRNA molecule and a homology sequence prediction (HSP) task for predicting whether two input mRNA sequences belong to organisms in a same homology class.

For the MLM learning task, the MLM loss function can be defined as $\mathcal{L}_{MLM} = \mathbb{E}_{x \sim X} \mathbb{E}_M \Sigma_{i \in M} -\log p(x_i | x_M)$, where X represents a batch of sequences, $p(x_i | x_M)$ represents a probability of the first machine-learning model predicting that a token $x_i$ is present at a particular masked position i, given an unmasked portion $x_M$ of the input sequence x.

For the HSP task, an HSP loss function can be defined as: $\mathcal{L}_{HSP} = -\mathbb{E}_N \Sigma_{n=1}^N [y_n \log p_n + (1-y_n) \log(1-p_n)]$, where $y_n$ represents a ground truth label of whether two input token sequences represent mRNA codon sequences belonging to a same homology class, and $p_n$ represents a predicted probability that the two input token sequences represent mRNA codon sequences belonging to the same homology class.

In an example implementation, 13 categories of mRNA sequences are used for the HSP task, including *E. coli, Homo sapiens* virus, two groups of mammalian (marsupials and monotremes), and 9 subgroups of placentals (primates, carnivores, rodents, even-toed ungulates, bats, odd-toed ungulates, insectivores, rabbits, more placentals). Two sequences that belong to the same category are considered homologous, otherwise not.

In some cases, to compute the HSP loss, the embedding model 220 takes a codon sequence pair as input and concatenates them with a separator token ([SEP]), and adds a classifier token ([CLS]) at the beginning of the combined sequence. The output embedding is used for computing a binary classification to predict whether the sequence pair are homologous sequences. The classification loss is computed based on the ground truth label.

The system 200 or another system can further include a supervised learning engine 260 configured to update the model parameters 232 of the prediction model 230 based on a labeled dataset 265. The labeled dataset 265 includes a plurality of labeled training examples. Each training example includes (i) a training input specifying a representation of a respective mRNA and (ii) a label specifying the property measure of the respective mRNA. The mRNA labels can be obtained based on experimental measurements of the properties of the corresponding mRNAs.

In general, the labeled dataset 265 includes a much fewer number of training sequences compared to the unlabeled dataset 255. In an illustrative example, while the unlabeled dataset 255 includes millions, tens of millions, or hundreds of millions of mRNA sequences, the labeled dataset 265 may include thousands, tens of thousands, or hundreds of thousands of labeled training examples. In a particular example, the labeled dataset 265 can include data from publicly available mRNA datasets providing diverse biophysical properties associated with these molecules.

For example, the labeled dataset 265 can include data from the mRFP Expression dataset, which provides protein production levels and the full coding sequences for several gene variants in *E. coli*. This data characterizes the randomization of codons across entire genes which can help to discover patterns and features correlated with translation efficiency, aiding in the design of synthetic genes optimized for enhanced protein expression. Further information of the mRFP Expression dataset can be found in "Revealing determinants of translation efficiency via whole-gene codon randomization and machine learning," Nieuwkoop et al., Nucleic Acids Research, 51(5):2363-2376, 012023.

The labeled dataset 265 can include data from the Fungal expression dataset, which includes protein-coding and tRNA genes from a wide range of fungal genomes. This data enables the discovery of common patterns of adaptive evolution throughout the fungal kingdom, offering insights into the evolutionary mechanisms and functional limitations that shape the evolution of fungal genes. Further information of the Fungal expression dataset can be found in "Kingdom-Wide Analysis of Fungal Protein-Coding and tRNA Genes Reveals Conserved Patterns of Adaptive Evolution," Wint et al., Molecular Biology and Evolution, 39(2), 01 2022. msab372.

The labeled dataset 265 can include data from heterologous proteins under the same expression condition in *E. coli* proteins and the corresponding experimental data. This data includes protein sequences, expression levels, and associated features, allowing insights into factors influencing expression efficiency. This data helps with optimizing protein production and understanding protein expression mechanisms. Further information of the heterologous proteins data can be found in "Mpepe, a predictive approach to improve protein expression in *E. coli* based on deep learning," Computational and Structural Biotechnology Journal, 20:1142-1153, 2022.

The labeled dataset 265 can include data from the Tc-Riboswitches dataset, which consists of a set of tetracycline (Tc) riboswitch dimers sequences upstream of a GFP protein. A riboswitch is a segment of mRNA that binds to small molecules, causing a change in the production of the proteins that mRNA encodes. Here only the 5' UTR region is changed while the GFP coding sequence remains the same. The measured variable in this dataset is the switching factor of a riboswitch which generally refers to the differential effect of the riboswitch in the presence or absence of its Tc. This data set is suitable for evaluating structural and confirmation dynamics of the 5' UTR region of mRNA constructs. Further information of the Tc-Riboswitches dataset can be found in "Tuning the performance of synthetic riboswitches using machine learning," Ann-Christin Groher, et al., ACS Synthetic Biology, 8(1):34-44, 2019.

The labeled dataset 265 can include data from the CoV2 Vaccine Degradation dataset, which encompasses a set of mRNA sequences that have been tuned for their structural features, stability, and translation efficiency, providing insights into designing more effective RNA-based treatments. Further information of the CoV2 Vaccine Degradation dataset can be found in "Combinatorial optimization of mrna structure, stability, and translation for rna-based therapeutics," Kathrin Leppek, et al., Nature Communications, 13(1):1536, 2022.

The supervised learning engine 260 is configured to perform supervised learning of a second machine-learning model including the prediction machine-learning model 230 on the labeled dataset 265. That is, the supervised learning engine 260 is configured to update the parameters of the second machine-learning model (including the model parameters 232 of the prediction machine-learning model 230) based on the labeled dataset 265.

The supervised learning engine 260 can update the parameters of the second machine-learning model (including model parameters 232 of the prediction machine-learning model 230) by minimizing a prediction error between the predicted mRNA property measure and the property measure specified in the labels. The supervised learning engine 260 can update the model parameters using any appropriate machine learning technique.

Based on the predicted mRNA property measure 240, the system 200 can select mRNA sequences with desirable properties from candidate mRNA sequences for a specific application. For example, the system 200 can generate an output that indicates whether a particular mRNA is suitable for a particular application, or an output that specifies the optimal mRNA sequence for the particular application. The system can transmit the output to a fabrication apparatus operative to implement the instruction to produce the mRNA.

Figure 2B:
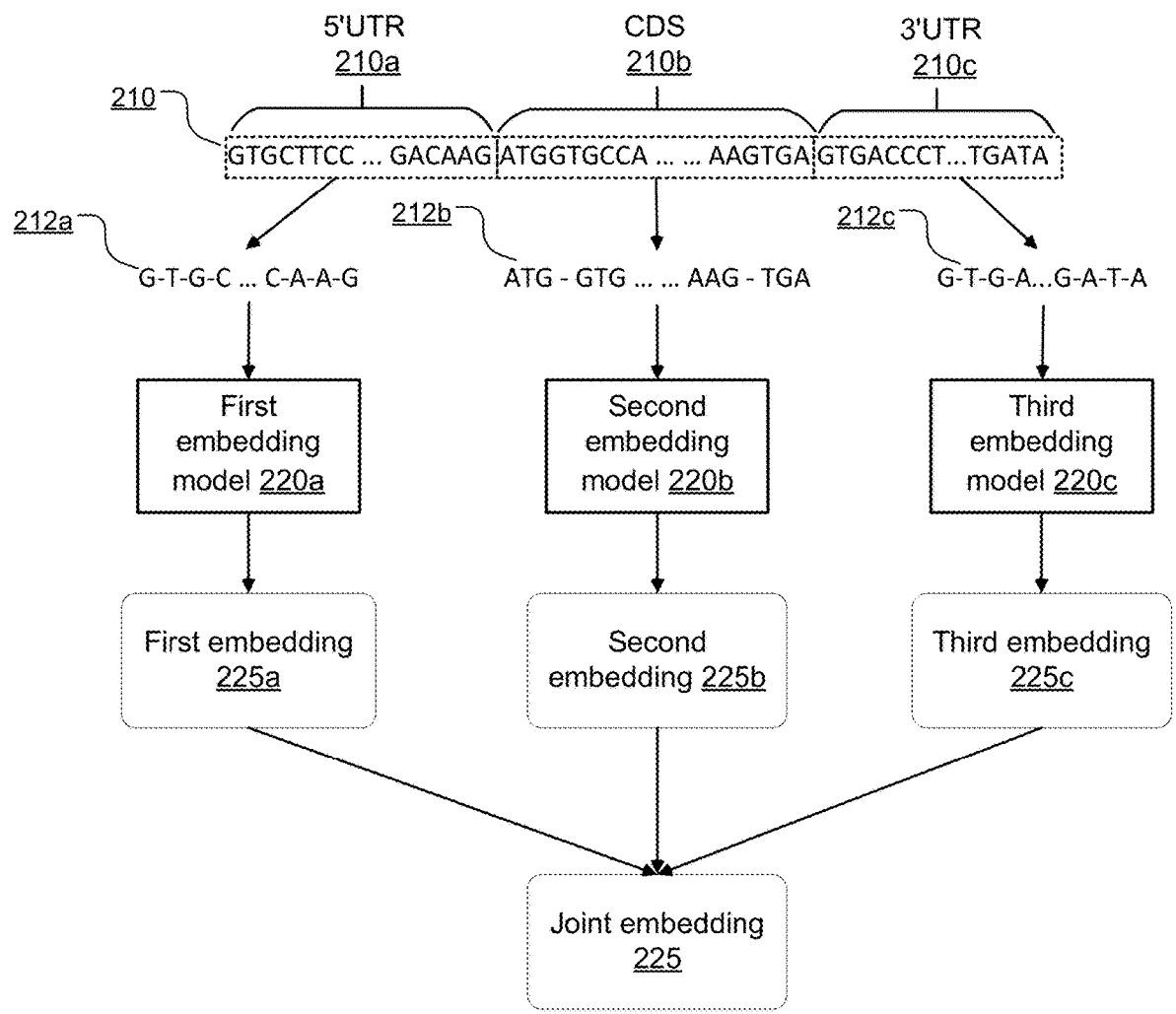
FIG. 2B illustrates an example process of generating embeddings for a full mRNA sequence.

FIG. 2B illustrates an example process of generating embeddings for a full mRNA sequence 210 that includes (i) a 5' UTR 210a, (ii) a CDS 210b, and (iii) a 3' UTR 210c. The system then numerically encodes the nucleotide sequence of the 5' UTR 212a into a first input token vector, the codon sequence of the CDS 212b into a second input token vector, and the nucleotide sequence of the 3' UTR 212c into a third input token vector. To generate the token vectors for the 3' and 5' UTRs, the system can map each nucleotide in the corresponding nucleotide sequence (212a or 212c) to a respective numerical value, and generate the input token vector by concatenating the numerical values. To generate the token vector for the CDS, the system can map each codon of the CDS codon sequence 212b to a respective numerical value, and generate the second input token vector by concatenating the numerical values.

To extract meaningful features from these encoded sequences, the system uses three distinct embedding machine-learning models 220a, 220b, and 220c, each configured to process one of the input token vectors. Specifically, the first embedding model 220a processes the 5' UTR input vector to generate a first embedded feature vector 225a, the second embedding model 220b processes the CDS input vector to generate a second embedded feature vector 225b, and the third embedding model 220c processes the 3' UTR input vector to generate a third embedded feature vector 225c.

The system then combines the first, second, and third feature vectors (225a-225c) into a joint embedding 225 as a representation of the entire mRNA molecule. For example, the system can perform pooling operations on these embedded feature vectors (225a-225c), and concatenate embeddings in the joint embedding 225. The joint embedding is to be processed by the property-prediction machine-learning model.

As will be further described with reference to FIG. 4B, the embedding models 210a-210b can be trained on a set of training mRNA sequences, e.g., a set of unlabeled mRNA sequences.

Further descriptions of the usage and training of machine-learning models for predicting mRNA molecule properties are provided below with references to FIGS. 3A-4B. Specifically, FIG. 3A and FIG. 4A illustrate the processes for using and training the machine-learning models to predict mRNA molecule properties based on the CDS codon sequence of the mRNA molecule.

Figure 3A:
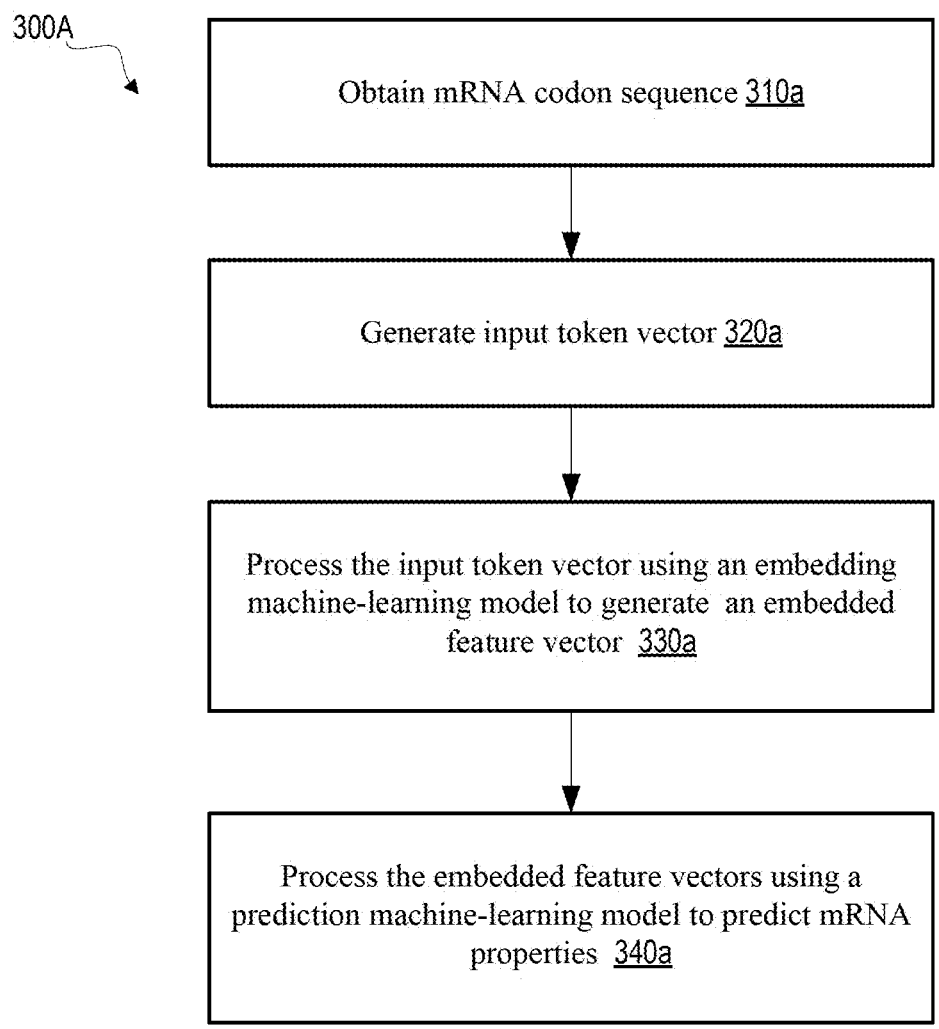
FIG. 3A is a flow diagram illustrating an example process for predicting a property of an mRNA sequence.
Figure 4A:
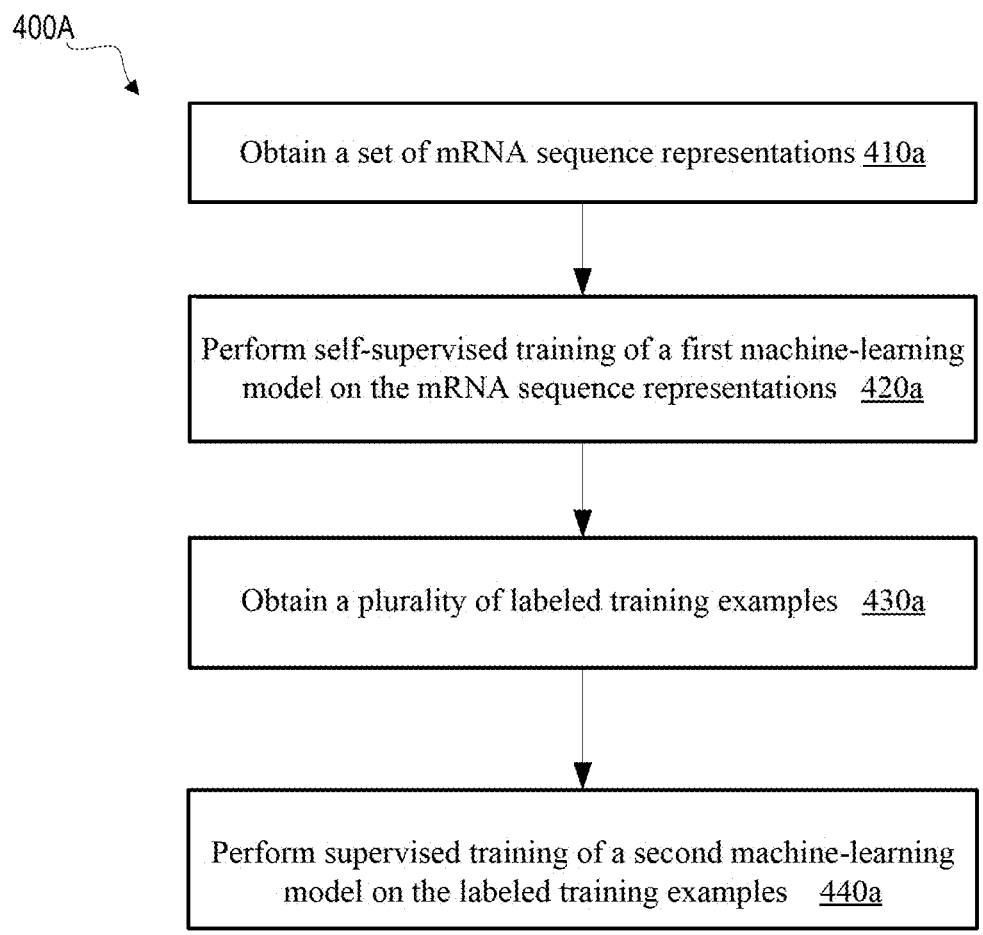
FIG. 4A is a flow diagram illustrating an example process for training a prediction model for predicting a property of mRNAs.

FIG. 3A is a flow diagram illustrating an example process 300A for predicting a property of an mRNA. For convenience, the process 300A will be described as being performed by a system of one or more computers located in one or more locations. For example, a property prediction system, e.g., the property prediction system 200 of FIG. 2A, appropriately programmed in accordance with this disclosure, can perform the process 300A.

At 310a, the system obtains an mRNA sequence, i.e., a token sequence representing the codon sequence of the mRNA. The mRNA sequence can be a sequence of a candidate mRNA that is intended for a particular application.

At 320a, the system generates an input token vector by numerically encoding the token sequence. For example, the system can generate a vector by concatenating numerical values assigned to different codons to form the input token vector.

At 330a, the system generates an embedded feature vector by processing the input token vector using an embedding machine-learning model. The embedding machine-learning model has a first set of model parameters. The first set of model parameters have been updated using a first training process of a first machine-learning model that comprises the embedding machine-learning model, wherein the first training process is performed based on a dataset specifying known codon sequences of mRNA molecules, and the first machine-learning model is configured to perform one or more pre-training tasks.

At 340a, the system processes an input including the embedded feature vector using a prediction machine-learning model to generate an output that predicts a property measure of the input mRNA. The property-prediction machine-learning model has a second set of model parameters that have been updated using a second training process, based on a plurality of training examples, of a second machine-learning model comprising the property-prediction machine-learning model. Each respective training example includes (i) a respective training input specifying a representation of a respective mRNA molecule and (ii) a respective label specifying one or more properties of the respective mRNA molecule.

In some cases, the process 300A can be used for selecting an mRNA molecule from a set of candidate mRNA molecules for performing a downstream task, e.g., to maximize an expression level of the mRNA in a specific type of cell or tissue or to maximize a stability of the mRNA in a specific environment. In particular, the system can predict properties of each of the candidate mRNA molecules using the processes described above, and select the mRNA molecule from the set of candidate mRNA molecules based on the predicted properties.

In some cases, the process 300A can be used to determine an optimal codon sequence of an mRNA molecule for performing a particular task. The system can maintain data representing a set of candidate sequences for the mRNA molecule and uses a reinforcement-learning (RL) model to process one or more of the candidate sequences to generate one or more new sequences. The RL model has been trained using a reward signal that includes mRNA molecule properties predicted using the process 300A. The system can select an optimal sequence from the new sequences.

To train the RL model, the system can use the RL model to process an input sequence representing an mRNA molecule to generate a set of one or more actions that modify the input sequence and determine a new sequence based on the input sequence and the set of actions. The system can compute one or more reward values indicative of how successfully the particular task is performed by an mRNA molecule represented by the new sequence, where the reward values can be computed using one or more mRNA molecule properties predicted using the process 300A. The system can adjust one or more parameters of the RL model based on at least the reward values.

FIG. 4A is a flow diagram illustrating an example process 400A for training a prediction model for predicting property measures of mRNAs. For convenience, the process 400A will be described as being performed by a system of one or more computers located in one or more locations. For example, a property prediction system, e.g., the property prediction system 200 of FIG. 2A, appropriately programmed in accordance with this disclosure, can perform the process 400A.

In general, the prediction model includes (i) an embedding machine-learning model configured to generate an embedded feature vector for a model input representing an codon sequence of the mRNA and (ii) a prediction machine-learning model configured to process the embedded feature vector to generate an output specifying a property measure of the mRNA.

At 410a, the system obtains a first dataset including a set of sequence representations of mRNAs. For example, the sequence representation can be a token vector that numerically encodes the codon sequence of a known mRNA sequence.

At 420a, the system performs self-supervised learning of a first machine-learning model including the embedding machine-learning model using the first data set. To perform the self-supervised learning, the system initiates values of the parameters of the first machine-learning model, and updates the values of the parameters of the first machine-learning model by minimizing a loss function defined for the one or more pre-training tasks.

In some cases, the pre-training tasks include a masked language model (MLM) learning task for predicting masked codons within a known mRNA molecule. In these cases, the loss function can include an MLM loss function defined as $\mathcal{L}_{MLM} = \mathbb{E}_{x \sim X} \mathbb{E}_M \Sigma_{i \in M} -\log p(x_i|x_M)$, where X represents a batch of sequences, $p(x_i|x_M)$ represents a probability of the first machine-learning model predicting that a token $x_i$ is present at a particular masked position i, given an unmasked portion $x_M$ of an input sequence x.

In some cases, the pre-training tasks includes a homology sequence prediction (HSP) task for predicting whether two input mRNA sequences belong to organisms in a same homology class. In these cases, the loss function can include an HSP loss function defined as: $\mathcal{L}_{HSP} = -\mathbb{E}_N \Sigma_{n=1}^N [y_n \log p_n + (1-y_n)\log(1-p_n)]$, where $y_n$ represents a ground truth label of whether two input token sequences represent mRNA codon sequences belonging to a same homology class, and $p_n$ represents a predicted probability that the two input token sequences represent mRNA codon sequences belonging to the same homology class.

In some cases, the loss function combines an MLM loss and an HSP loss.

At 430a, the system obtains a second dataset including a plurality of training examples. Each training example includes (i) a respective training input specifying a representation of a respective mRNA and (ii) (ii) a respective label characterizing one or more properties of the respective mRNA molecule.

At 440a, the system performs supervised learning of a second machine-learning model including the prediction machine-learning model based on the second dataset. The second machine-learning model can include one or more of: a neural network, a K-nearest neighbors model, a support vector machine, a decision trees model, a random forest model, or a ridge regression model.

Figure 3B:
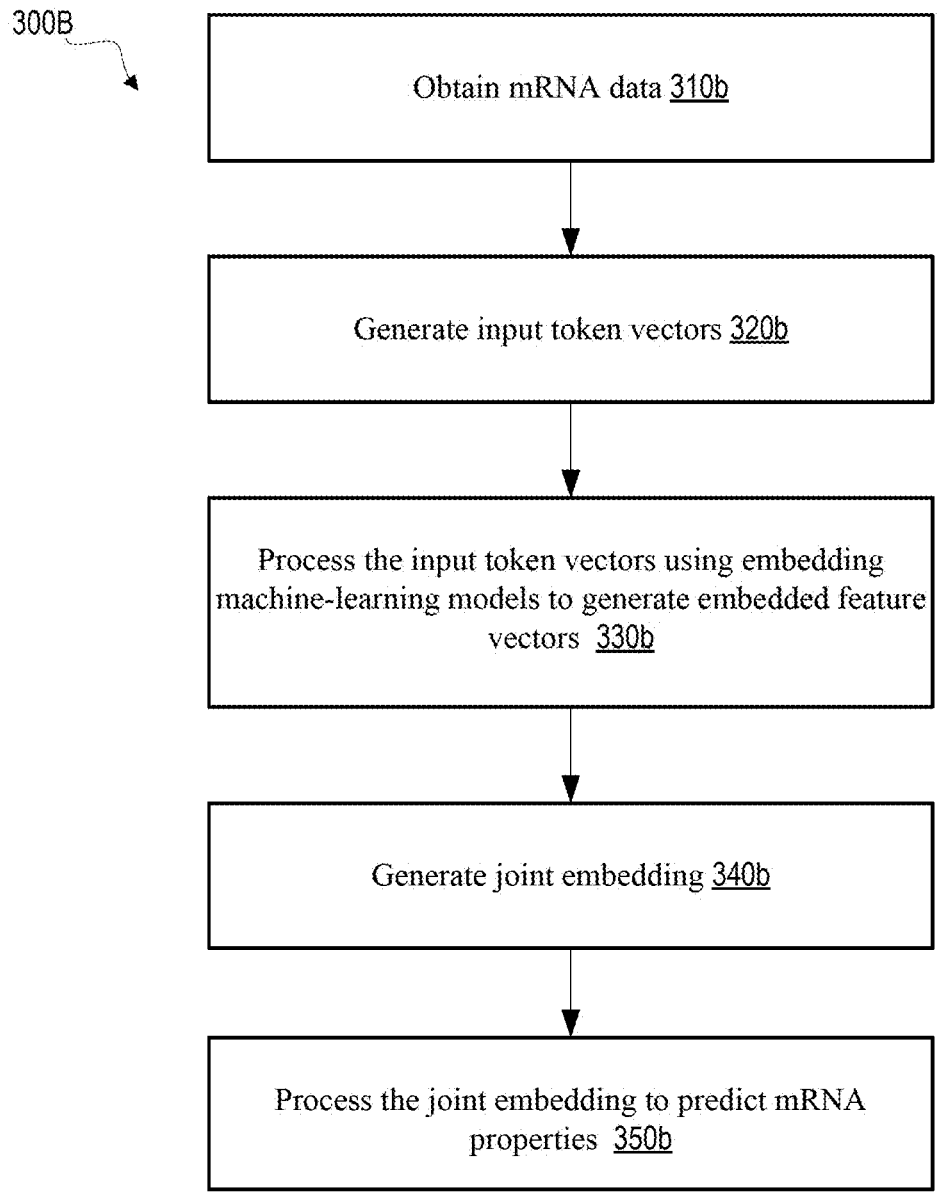
FIG. 3B is a flow diagram illustrating another example process 300B for predicting a property of an mRNA.
Figure 4B:
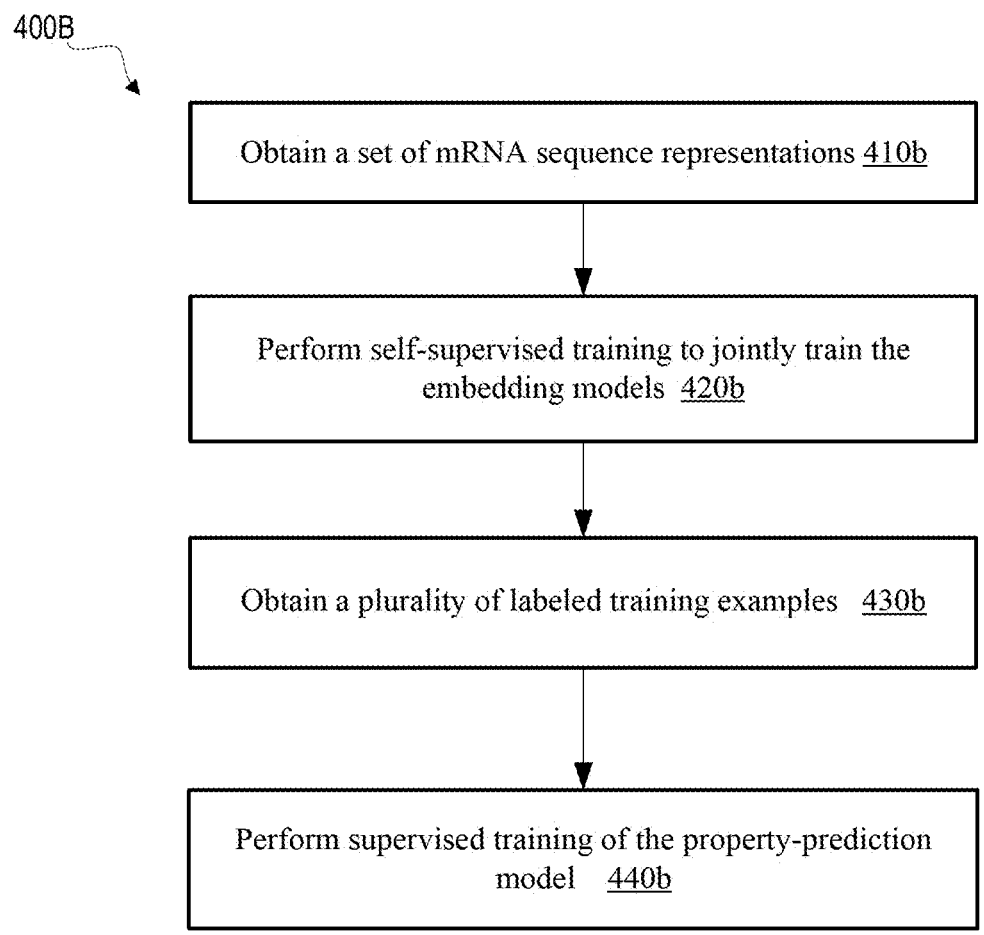
FIG. 4B is a flow diagram illustrating an example process for training a prediction model for predicting property measures of mRNAs.

The description with references FIG. 3B and FIG. 4B provided below illustrate the processes for using and training the machine-learning models to predict mRNA molecule properties from the full mRNA sequence, including the 5' UTR, CDS, and 3' UTR.

FIG. 3B is a flow diagram illustrating another example process 300B for predicting a property of an mRNA. For convenience, the process 300B will be described as being performed by a system of one or more computers located in one or more locations. For example, a property prediction system, e.g., the property prediction system 200 of FIG. 2A, appropriately programmed in accordance with this disclosure, can perform the process 300B.

At 310b, the system obtains data representing an mRNA molecule. The mRNA molecule includes (i) a 5' untranslated region (UTR), (ii) a coding sequence (CDS), and (iii) a 3' UTR. The mRNA sequence can be a sequence of a candidate mRNA that is intended for a particular application.

At 320b, the system generates a first input token vector by numerically encoding a nucleotide sequence of the 5' UTR of the mRNA molecule, generates a second input token vector by numerically encoding a codon sequence of the CDS of the mRNA molecule, and generates a third input token vector by numerically encoding a nucleotide sequence of the 3' UTR of the mRNA molecule. For example, the system can generate the first input token vector by mapping each nucleotide of the nucleotide sequence of the 5' UTR to a respective numerical value concatenating the numerical values. The system can generate the second input token vector by mapping each codon of the codon sequence of the CDS to a respective numerical value concatenating the numerical values. The system can generate the third input token vector by mapping each nucleotide of the nucleotide sequence of the 3' UTR to a respective numerical value and concatenating the numerical values.

At 330b, the system generates a first embedded feature vector by processing the first input token vector using a first embedding machine-learning model, generates a second embedded feature vector by processing the second input token vector using a second embedding machine-learning model, and generates a third embedded feature vector by processing the third input token vector using a third embedding machine-learning model. Before using the first, the second, and the third embedding machine-learning models for generating the embedding feature vectors, the system or another system can train the models on a set of training mRNA sequences using a first training process. The first training process is described in further detail with reference to FIG. 4B. In some cases, each of the first, the second, and the third embedding machine-learning models includes a respective large language model (LLM). For example, each of the first, the second, and the third embedding machine-learning models includes a respective bidirectional transformer.

At 340b, the system generates a joint embedding by combining the first embedded feature vector, the second embedded feature vector, and the third embedded feature vector. In some implementations, to generate the joint embedding, the system performs a first pooling operation on the first embedded feature vector to generate a first embedding, performs a second pooling operation on the second embedded feature vector to generate a second embedding, performs a third pooling operation on the third embedded feature vector to generate a third embedding, and concatenates the first embedding, the second embedding, and the third embedding to generate the joint embedding.

At 350b, the system processes the joint embedding using a property-prediction machine-learning model to generate an output that predicts one or more properties of the mRNA molecule. Before using the property-prediction machine-learning model to generate the output, the system or another system can train the property-prediction machine-learning model on a set of labeled training examples using a second training process. The second training process is described in further detail with reference to FIG. 4B.

In some cases, the process 300B can be used for selecting an mRNA molecule from a set of candidate mRNA molecules for performing a downstream task, e.g., to maximize an expression level of the mRNA in a specific type of cell or tissue or to maximize a stability of the mRNA in a specific environment. In particular, the system can predict properties of each of the candidate mRNA molecules using the processes described above, and select the mRNA molecule from the set of candidate mRNA molecules based on the predicted properties.

In some cases, the process 300B can be used to determine an optimal sequence of an mRNA molecule for performing a particular task. The system can maintain data representing a set of candidate sequences for the mRNA molecule and uses a reinforcement-learning (RL) model to process one or more of the candidate sequences to generate one or more new sequences. The RL model has been trained using a reward signal that includes mRNA molecule properties predicted using the process 300B. The system can select an optimal sequence from the new sequences.

To train the RL model, the system can use the RL model to process an input sequence representing an mRNA molecule to generate a set of one or more actions that modify the input sequence and determine a new sequence based on the input sequence and the set of actions. The system can compute one or more reward values indicative of how successfully the particular task is performed by an mRNA molecule represented by the new sequence, where the reward values can be computed using one or more mRNA molecule properties predicted using the process 300A. The system can adjust one or more parameters of the RL model based on at least the reward values.

FIG. 4B is a flow diagram illustrating an example process 400B for training a prediction model for predicting property measures of mRNAs. For convenience, the process 400B will be described as being performed by a system of one or more computers located in one or more locations. For example, a property prediction system, e.g., the property prediction system 200 of FIG. 2A, appropriately programmed in accordance with this disclosure, can perform the process 400A.

In general, the mRNA molecule includes (i) a 5' untranslated region (UTR), (ii) a coding sequence (CDS), and (iii) a 3' UTR. The prediction model includes (i) a first embedding machine-learning model configured to process a first input token vector representing a nucleotide sequence of the 5' UTR of the mRNA molecule to generate a first embedded feature vector, (ii) a second embedding machine-learning model configured to process a second input token vector representing a codon sequence of the mRNA molecule to generate a second embedded feature vector, (iii) a third embedding machine-learning model configured to process a third input token vector representing a nucleotide sequence of the 3' UTR of the mRNA molecule to generate a third embedded feature vector, and (iv) a property-prediction machine-learning model configured to process a joint embedding generated by combining the first, the second, and the third embedded feature vector to generate an output specifying one or more properties of the mRNA molecule.

At 410b, the system obtains a first dataset including a set of sequence representations of mRNAs. For example, each mRNA sequence representation can include a first token vector that numerically encodes the nucleotide sequence of the 5' UTR of a known mRNA molecule, a second token vector that numerically encodes the CDS codon sequence of the known mRNA sequence, and a third token vector that numerically encodes the nucleotide sequence of the 3' UTR of the known mRNA molecule.

At 420b, the system performs self-supervised learning to train the first, the second, and the third embedding machine-learning models on one or more pre-training tasks using the first data set. To perform the self-supervised learning, the system can initiate values of parameters of a first machine-learning model including the first, the second, and the third embedding machine-learning models, then train the first machine-learning model by minimizing one or more pre-training loss function including one or more pre-training losses defined for one or more pre-training tasks.

In some cases, the first, the second, and the third embedding machine-learning models are jointly trained. That is, the system can update the parameters of these models by minimizing a joint loss function that combines at least the pre-training losses computed for each of the first, the second, and the third embedding machine-learning models.

In some other cases, in order to improve computational efficiency, the first, the second, and the third embedding machine-learning models are separately trained. That is, the system updates the parameters of each particular embedding model by minimizing a loss function for the particular model.

In some cases, the pre-training tasks include a masked language model (MLM) learning task for predicting masked tokens within a known mRNA molecule. In these cases, the loss function can include an MLM loss function defined as $\mathcal{L}_{MLM} = \mathbb{E}_{x \sim X} \mathbb{E}_{M} \Sigma_{i \in M} -\log p(x_i | x_M)$, where X represents a batch of sequences, $p(x_i | x_M)$ represents a probability of the first machine-learning model predicting that a token $x_i$ is present at a particular masked position i, given an unmasked portion $x_M$ of an input sequence x.

In some cases, the pre-training tasks includes a homology sequence prediction (HSP) task for predicting whether two input mRNA sequences belong to organisms in a same homology class. In these cases, the loss function can include an HSP loss function defined as: $\mathcal{L}_{HSP} = -\mathbb{E}_N \Sigma_{n=1}^{N} [y_n \log p_n + (1 - y_n) \log(1 - p_n)]$, where $y_n$ represents a ground truth label of whether two input token sequences represent mRNA sequences belonging to a same homology class, and $p_n$ represents a predicted probability that the two input token sequences represent mRNA sequences belonging to the same homology class.

In some cases, the loss function combines an MLM loss and an HSP loss.

At 430b, the system obtains a second dataset including a plurality of training examples. Each training example includes (i) a respective training input specifying a representation of a respective mRNA molecule and (ii) a respective label characterizing one or more properties of the respective mRNA molecule.

At 440b, the system performs supervised learning to train the property-prediction machine-learning model on one or more property prediction tasks using the second dataset. The second machine-learning model can include one or more of: a neural network, a K-nearest neighbors model, a support vector machine, a decision trees model, a random forest model, or a ridge regression model. To train the property-prediction machine-learning model, the system can initiate values of parameters of a second machine-learning model that includes the property-prediction machine-learning model, and train the second machine-learning model by minimizing a downstream loss function comprising one or more prediction losses defined for one or more property prediction tasks.

In some implementations, the downstream training for the property-prediction machine-learning model is performed such that the parameters of the embedding models are fixed at the values obtained through self-supervised pre-training. That is, the parameters of the embedding models are not updated during the supervised downstream training. This approach leverages the embedding process learned during pre-training without modifying it further.

In some other implementations, the parameter values of the embedding models are updated during the supervised downstream training. In these cases, the parameters of the embedding models are further fine-tuned for each downstream task, potentially leading to improved performance at inference. However, updating all parameters of both the embedding models and the prediction model during downstream training can require large computing resources, especially for large models. For example, in some cases, the combined model, which integrates the embedding models and the property-prediction model, can include hundreds of millions of parameters. This can require substantial computing resources, longer training times, and increased energy consumption.

To address these challenges, the system can use techniques such as Low-Rank Adaptation (LoRA), which allows selective fine-tuning of a smaller subset of parameters in the model, thereby enhancing training efficiency and reducing the risk of overfitting while maintaining robust model performance. In particular, in LoRA, the system inserts trainable rank decomposition matrices into each transformer layer of the embedding models, while keeping the parameters of the originally pre-trained embedding models fixed during downstream training.

In an example of implementing LoRA, the system injects two fully-connected layers with size $d_{in} \times r$ and $d_{out} \times r$, respectively, where $d_{in}$ and $d_{out}$ are the hidden and intermediate sizes of the pre-trained embedding models, and r is the LoRA rank, which is a hyper-parameter affecting the number of weights. In an illustrative example, the $d_{in}$ and $d_{out}$ are 764 and 3072, respectively for all 12 layers. The system uses a rank of 32 for LoRA resulting in a total of $(768+3072) \times 12 \times 32 = 1474560$ tuned parameters, which can be less than 2% of the total parameters in the pre-trained embedding models.

In some implementations, the system can further incorporate a contrastive loss in the pre-training of the embedding models or the downstream training of the property prediction model. The contrastive loss aims to maximize similarities between embeddings of different regions within a same mRNA sequence while minimizing the similarities between the embeddings of different regions from different mRNA sequence, and can be incorporated in the pre-training loss function or the downstream loss function.

ISI, the contrastive loss $\mathcal{L}_C$ includes a first contrastive loss $\mathcal{L}_{C1}$ that aims to maximize the similarity between the embeddings of the 5' UTR and the CDS within the same mRNA sequence while minimizing the similarity between the embeddings of the 5' UTR and the CDS from two different mRNA sequences. In some cases, the contrastive loss $\mathcal{L}_C$ includes a first contrastive loss $\mathcal{L}_{C2}$ that aims to maximize the similarity between the embeddings of the 3' UTR and the CDS within the same mRNA sequence while minimizing the similarity between the embeddings of the 3' UTR and the CDS from two different mRNA sequences.

As an illustrative example, the first and/or the second contrastive losses can be computed by $$\mathcal{L}_{C1,2} = -\frac{1}{N}\sum_{i=1}^{N} \log \frac{\exp\left(sim(u_i, v_i)/\tau\right)}{\sum_{j=1}^{N} \exp\left(sim(u_i, v_j)/\tau\right)},$$

where N is the batch size of a batch of training examples, u is a normalized embedding generated for a 5' UTR (in the case of computing $\mathcal{L}_{C1}$), or for a 3'UTR (in the case of computing $\mathcal{L}_{C2}$). v is a normalized embedding generated for a CDS. sim(.,.) is the cosine similarity, and i is a temperature parameter.

In some cases, the contrastive loss can be computed as a combined contrastive loss that combines the first contrastive loss and the second contrastive loss. For example, the combined contrastive loss can be computed as an average of the first contrastive loss and the second contrastive loss, that is, $\mathcal{L}_C = (\mathcal{L}_{C1} + \mathcal{L}_{C2})/2$.

In some cases, the system can incorporate the contrastive loss into the downstream training of the property prediction model by including the contrastive loss in the downstream loss function. For example, the downstream loss function can be computed as $\mathcal{L}_{downsstream} = \mathcal{L}_{prediction} + \alpha \mathcal{L}_C$, where $\alpha$ is an adjustment coefficient.

In some other cases, the system can incorporate the contrastive loss into the pre-training training of the embedding models by including the contrastive loss in the pre-training loss function. For example, when the first, the second, and the third embedding machine-learning models are jointly trained, the system can incorporate the contrastive loss into the joint loss function. In another example, when the first, the second, and the third embedding machine-learning models are separately trained, the system can incorporate the contrastive loss into the loss function for the second embedding machine-learning model that generates the embeddings for the CDS.

Figure 5:
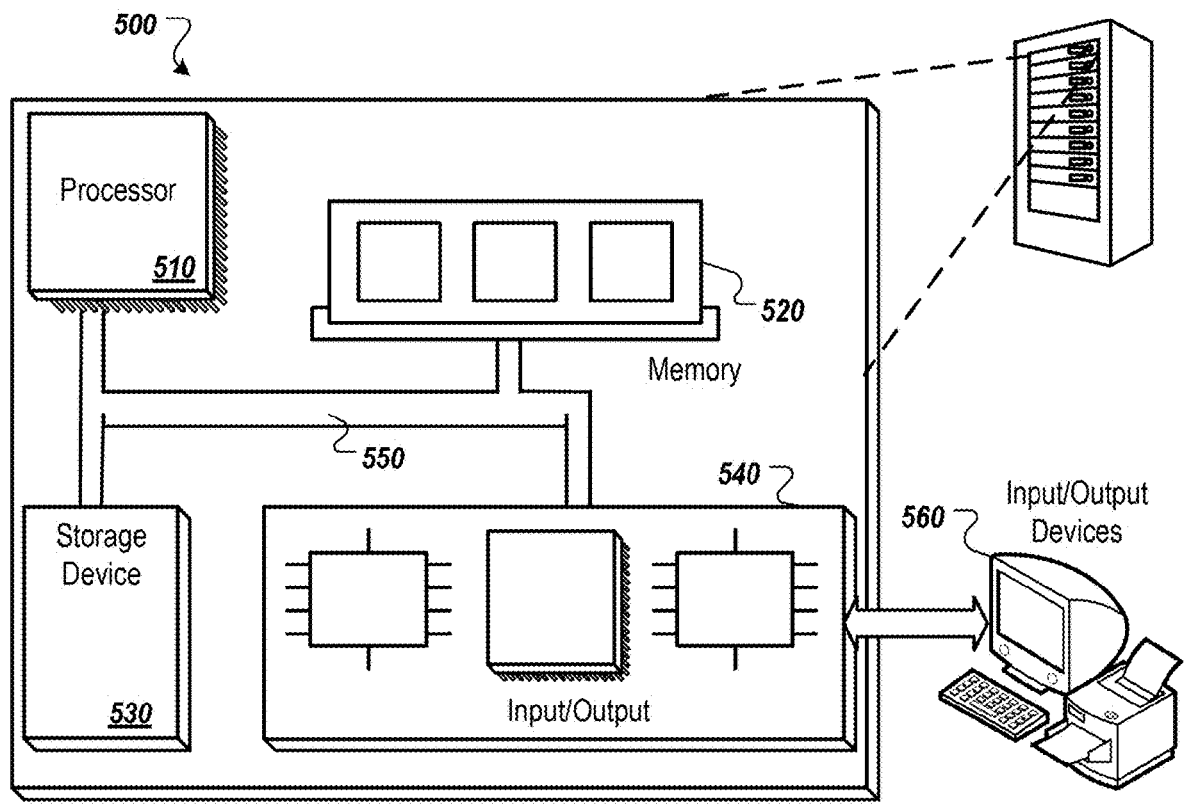
FIG. 5 is a block diagram of an example computer system.

FIG. 5 is a block diagram of an example computer system 500 that can be used to perform operations described above. The system 500 includes a processor 510, a memory 520, a storage device 530, and an input/output device 540. Each of the components 510, 520, 530, and 540 can be interconnected, for example, using a system bus 550. The processor 510 is capable of processing instructions for execution within the system 500. In one implementation, the processor 510 is a single-threaded processor. In another implementation, the processor 510 is a multi-threaded processor. The processor 510 is capable of processing instructions stored in the memory 520 or on the storage device 530.

The memory 520 stores information within the system 500. In one implementation, the memory 520 is a computer-readable medium. In one implementation, the memory 520 is a volatile memory unit. In another implementation, the memory 520 is a non-volatile memory unit.

The storage device 530 is capable of providing mass storage for the system 500. In one implementation, the storage device 530 is a computer-readable medium. In various different implementations, the storage device 530 can include, for example, a hard disk device, an optical disk device, a storage device that is shared over a network by multiple computing devices (for example, a cloud storage device), or some other large capacity storage device.

The input/output device 540 provides input/output operations for the system 500. In one implementation, the input/output device 540 can include one or more network interface devices, for example, an Ethernet card, a serial communication device, for example, a RS-232 port, and/or a wireless interface device, for example, a 502.11 card. In another implementation, the input/output device can include driver devices configured to receive data and send output data to other input/output devices, for example, keyboard, printer and display devices 560. Other implementations, however, can also be used, such as mobile computing devices, mobile communication devices, set-top box television client devices, etc.

Although an example processing system has been described in FIG. 5, implementations of the subject matter and the functional operations described in this disclosure can be implemented in other types of digital electronic circuitry, or in computer software, firmware, or hardware, including the structures disclosed in this disclosure and their structural equivalents, or in combinations of one or more of them.

Figure 6:
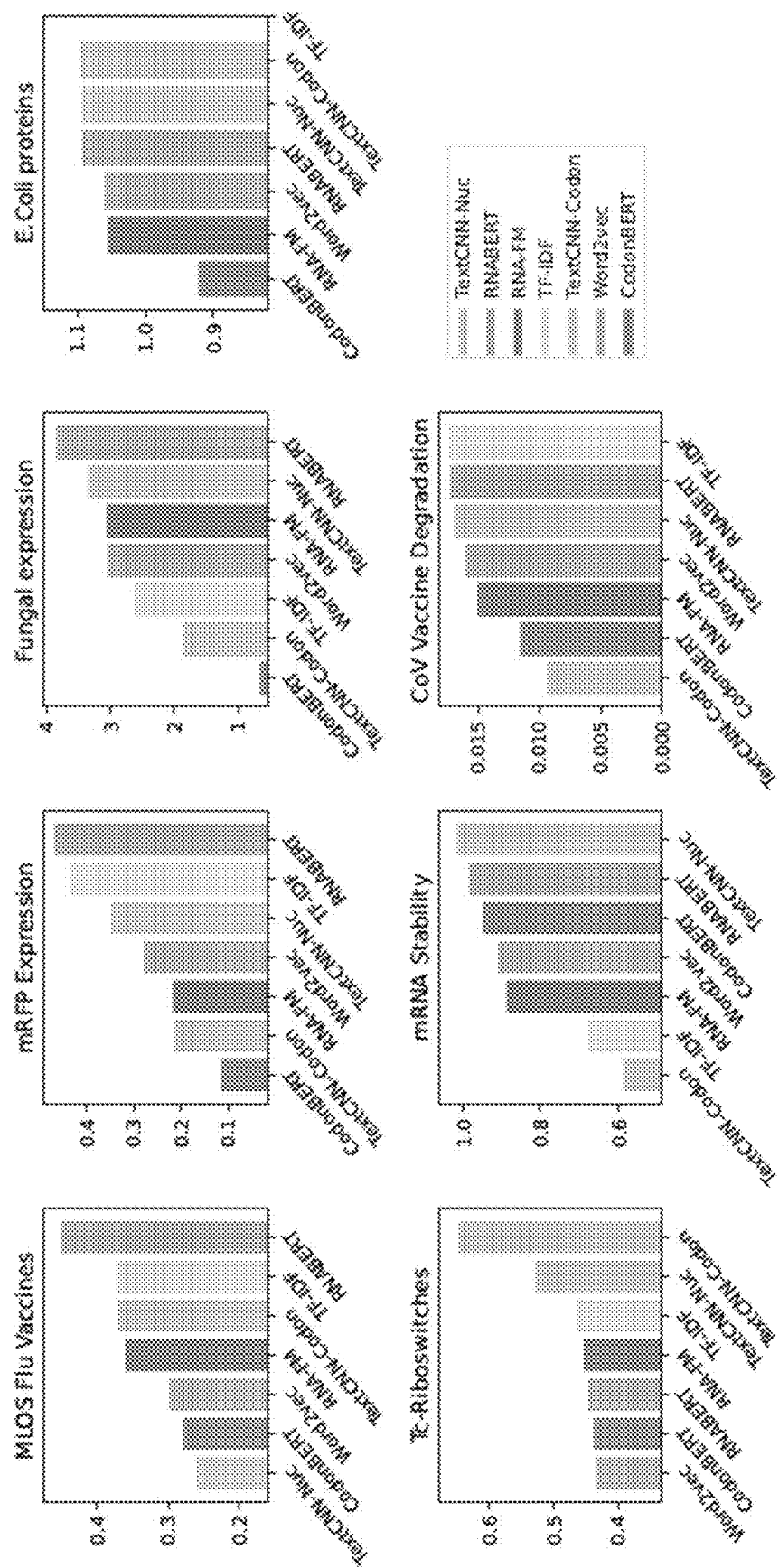
FIG. 6 shows a performance comparison of different mRNA property prediction models for a variety of prediction tasks.

FIG. 6 shows a performance comparison of different mRNA property prediction models for a variety of prediction tasks. The performances are measured by root mean squared errors (RMSEs) of the prediction result compared to benchmark data.

These models include a "CodonBERT" model, which includes a BERT model for encoding mRNA codon sequences and a downstream prediction model. The embedding models for embedding the 3' and 5' UTRs are not included in this model. The "RNABERT" model includes a BERT model for encoding mRNA nucleotide sequences. The "TextCNN-Nuc" model uses a Convolutional Neural Network (CNN) to process mRNA nucleotide sequences. The "TextCNN-codon" model uses a CNN to process mRNA codon sequences. As shown in FIG. 6, CodonBERT outperforms other models on protein expression tasks, which demonstrates the efficacy of the disclosed method.

FIG. 7 shows another performance comparison of different mRNA property prediction models for a variety of prediction tasks. The performances are measured by the Spearman correlation coefficients or the Area Under the Receiver Operating Characteristic Curve (AUROC).

These models include a "mRNA-LM" model, which includes a first BERT model for encoding 5' UTRs, a second BERT model for encoding mRNA codon sequences, a third BERT model for encoding 3'UTRs, and a downstream prediction model. The "RNA-FM" model is described in Chen, et al., "Interpretable RNA foundation model from unannotated data for highly accurate RNA structure and function", arXiv:2204.00300, 2022. The "Saluki" model is described in Agarwal et al., "The genetic and biochemical determinants of mRNA degradation rates in mammals", Genome Biology", 23(1), 245, 2022. As shown in FIG. 7, mRNA-LM outperforms other models on for predicting mRNA half-life, translation rate, transcript expression, and protein expression. This comparison demonstrates the efficacy of the disclosed method.

This disclosure uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions. Embodiments of the subject matter and the functional operations described in this disclosure can be implemented in digital electronic circuitry, in tangibly-embodied computer software or firmware, in computer hardware, including the structures disclosed in this disclosure and their structural equivalents, or in combinations of one or more of them. Embodiments of the subject matter described in this disclosure can be implemented as one or more computer programs, i.e., one or more modules of computer program instructions encoded on a tangible non transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a data communication network.

In this disclosure, the term "database" is used broadly to refer to any collection of data: the data does not need to be structured in any particular way, or structured at all, and it can be stored on storage devices in one or more locations. Thus, for example, the index database can include multiple collections of data, each of which may be organized and accessed differently.

Similarly, in this disclosure the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this disclosure can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks.

To provide for interaction with a user, embodiments of the subject matter described in this disclosure can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., the PyTorch, Scikit-learn, Keras, or TensorFlow framework.

Embodiments of the subject matter described in this disclosure can be implemented in a computing system that includes a back end component, e.g., as a data server, or that includes a middleware component, e.g., an application server, or that includes a front end component, e.g., a client computer having a graphical user interface, a web browser, or an app through which a user can interact with an implementation of the subject matter described in this disclosure, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this disclosure contains many specific implementation details, these should not be construed as limitations on the scope of any invention or on the scope of what may be claimed, but rather as descriptions of features that may be specific to particular embodiments of particular inventions. Certain features that are described in this disclosure in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

The invention claimed is:

1. A computer-implemented method for predicting properties of an mRNA molecule, the method comprising:
   obtaining data representing (i) a codon sequence of a coding sequence (CDS) of the mRNA molecule and (ii)

a respective nucleotide sequence of each of one or more non-coding regions of the mRNA molecule;

generating an input token vector by numerically encoding the codon sequence;

generating an embedded feature vector for the CDS of the mRNA molecule by processing the input token vector using an embedding neural network, wherein the embedding neural network has the first set of model parameters that have been updated using a first training process of a first neural network, wherein the first training process is performed based on a dataset specifying known codon sequences of mRNA molecules, and the first neural network is configured to perform one or more pre-training tasks;

generating a joint embedding by combining the embedded feature vector generated for the CDS of the mRNA molecule with one or more embeddings generated from the nucleotide sequences of the one or more non-coding regions of the mRNA molecule;

processing the joint embedding using a property-prediction machine-learning model to generate an output that predicts one or more properties of the mRNA molecule, wherein the property-prediction machine-learning model has a second set of model parameters that have been updated using a second training process of a machine-learning model, wherein the second training process is based on a plurality of training examples, each training example comprising (i) a respective training input specifying a representation of a respective mRNA molecule and (ii) a respective label specifying one or more properties of the respective mRNA molecule; and providing the one or more predicted properties of the mRNA molecule for physically generating the mRNA molecule.

2. The method of claim 1, wherein generating the input token vector comprises: mapping each codon of the codon sequence to a respective numerical value; and generating the input token vector by concatenating the respective numerical values.

3. The method of claim 1, wherein the first training process comprises:

initiating values of parameters of the first neural network; and updating the values of the parameters of the first neural network by minimizing a loss function defined for the one or more pre-training tasks.

4. The method of claim 3, wherein the one or more pre-training tasks include a masked language model (MLM) learning task for predicting masked codons within a known mRNA molecule.

5. The method of claim 3, wherein the one or more pre-training tasks include a homology sequence prediction (HSP) task for predicting whether two input mRNA sequences belong to organisms in a same homology class.

6. The method of claim 3, wherein the loss function combines an MLM loss and an HSP loss.

7. The method of claim 1, wherein the one or more properties of the mRNA molecule comprises expression level of the mRNA molecule in a specific type of cell or tissue.

8. The method of claim 7, wherein the mRNA molecule is a component of a vaccine and is encoded for expressing an antigenic protein of a target pathogen, and the one or more predicted properties of the mRNA molecule comprises expression levels of the antigenic protein of the target pathogen in the specific type of cell or tissue.

9. The method of claim 1, wherein the one or more properties of the mRNA molecule comprises a stability under one or more environmental conditions.

10. The method of claim 1, wherein the one or more properties of the mRNA molecule comprises a switching factor of the mRNA molecule in a specific type of cell or tissue.

11. The method of claim 1, wherein the one or more properties of the mRNA molecule comprises a degradation rate of the mRNA molecule under one or more environmental conditions.

12. The method of claim 11, wherein the mRNA molecule is a component of a SARS-CoV-2 vaccine, and the property-prediction machine-learning model is configured to predict the degradation rate of the mRNA molecule under physiological conditions.

13. The method of claim 1, wherein the first neural network comprises a large language model (LLM).

14. The method of claim 1, wherein the first neural network comprises a bidirectional transformer.

15. A method for selecting an mRNA molecule from a set of candidate mRNA molecules for performing a downstream task, the method comprising:

predicting properties of each of the set of candidate mRNA molecules using the method of claim 1; and selecting the mRNA molecule from the set of candidate mRNA molecules based on the predicted properties.

16. The method of claim 15, further comprising:

physically generating the selected mRNA molecule.

17. A computer-implemented method for training a prediction model for predicting properties for an mRNA molecule, wherein the prediction model includes (i) an embedding neural network configured to generate an embedded feature vector for a model input representing a codon sequence of a coding sequence (CDS) of the mRNA molecule and (ii) a property-prediction machine-learning model configured to process a joint embedding generated by combining the embedded feature vector generated for the CDS of the mRNA molecule with one or more embeddings generated from nucleotide sequences of one or more non-coding regions of the mRNA molecule to generate an output specifying one or more properties of the mRNA molecule, the method comprising:

obtaining a first dataset comprising a set of sequence representations of mRNA molecules;

training a first neural network comprising the embedding neural network on one or more pre-training tasks using the first dataset;

obtaining a second dataset comprising a plurality of training examples, each respective training example comprising (i) a respective training input specifying a representation of a respective mRNA molecule and (ii) a respective label characterizing one or more properties of the respective mRNA molecule;

performing supervised learning of a machine-learning model comprising the property-prediction machine-learning model on the second dataset; and providing data specifying the trained prediction model to an mRNA property prediction system for predicting one or more properties of the mRNA molecule.

18. The method of claim 17, wherein training the first neural network comprises:

initiating values of parameters of the first neural network; and updating the values of the parameters of the first neural network by minimizing a loss function defined for the one or more pre-training tasks.

19. The method of claim 18, wherein the one or more pre-training tasks include a masked language model (MLM) learning task for predicting masked codons within a known mRNA molecule.

20. The method of claim 18, wherein the loss function comprises an MLM loss function defined as:

$$\mathcal{L}_{MLM} = \mathbb{E}_{x \sim X} \mathbb{E}_M \sum_{i \in M} -\log p(x_i \mid x_M),$$

where X represents a batch of sequences, p (x_i|x_M) represents a probability of the first neural network predicting that a token $x_i$ is present at a particular masked position i, given an unmasked portion $x_M$ of an input sequence x.

21. The method of claim 18, wherein the one or more pre-training tasks include a homology sequence prediction (HSP) task for predicting whether two input mRNA sequences belong to organisms in a same homology class.

22. The method of claim 21, wherein the loss function comprises an HSP loss function defined as:

$$\mathcal{L}_{HSP} = -\mathbb{E}_N \sum_{n=1}^{N} [y_n \log p_n + (1 - y_n)\log(1 - p_n)],$$

where $y_n$ represents a ground truth label of whether two input token sequences represent mRNA codon sequences belonging to a same homology class, and $p_n$ represents a predicted probability that the two input token sequences represent mRNA codon sequences belonging to the same homology class.

23. The method of claim 18, wherein the loss function combines an MLM loss and an HSP loss.

24. The method of claim 23, wherein the one or more properties of the mRNA molecule comprises one or more of:
  expression level of the mRNA molecule in a specific type of cell or tissue;
  stability under one or more environmental conditions;
  or switching factor of the mRNA molecule in a specific type of cell or tissue.

25. The method of claim 17, wherein the first neural network comprises a large language model (LLM).

26. The method of claim 17, wherein the neural network comprises a bidirectional transformer.

27. A system comprising:
  one or more computers; and
  one or more storage devices storing instructions that when executed by the one or more computers, cause the one or more computers to perform operations comprising:
  obtaining data representing (i) a codon sequence of a coding sequence (CDS) of a mRNA molecule and (ii) a respective nucleotide sequence of each of one or more non-coding regions of the mRNA molecule;
  generating an input token vector by numerically encoding the codon sequence;
  generating an embedded feature vector for the CDS of the mRNA molecule by processing the input token vector using an embedding neural network having a first set of model parameters, wherein the embedding neural network has the first set of model parameters that have been updated using a first training process of a first neural network, wherein the first training process is performed based on a dataset specifying known codon sequences of mRNA molecules, and the first neural network is configured to perform one or more pre-training tasks;
  generating a joint embedding by combining the embedded feature vector generated for the CDS of the mRNA molecule with one or more embeddings generated from the nucleotide sequences of the one or more non-coding regions of the mRNA molecule;
  processing the joint embedding using a property-prediction machine-learning model to generate an output that predicts one or more properties of the mRNA molecule, wherein the property-prediction machine-learning model has a second set of model parameters that have been updated using a second training process of a machine-learning model, wherein the second training process is based on a plurality of training examples, each training example comprising (i) a respective training input specifying a representation of a respective mRNA molecule and (ii) a respective label specifying one or more properties of the respective mRNA molecule; and
  providing the one or more predicted properties of the mRNA molecule for physically generating the mRNA molecule.

28. One or more non-transitory computer-readable storage media storing instructions that, when executed by one or more computers, cause the one or more computers to perform operations comprising:
  one or more computers; and
  one or more storage devices storing instructions that when executed by the one or more computers, cause the one or more computers to perform operations comprising:
  obtaining data representing (i) a codon sequence of a coding sequence (CDS) of a mRNA molecule and (ii) a respective nucleotide sequence of each of one or more non-coding regions of the mRNA molecule;
  generating an input token vector by numerically encoding the codon sequence;
  generating an embedded feature vector for the CDS of the mRNA molecule by processing the input token vector using an embedding neural network having a first set of model parameters, wherein the embedding neural network has the first set of model parameters that have been updated using a first training process of a first neural network, wherein the first training process is performed based on a dataset specifying known codon sequences of mRNA molecules, and the first neural network is configured to perform one or more pre-training tasks;
  generating a joint embedding by combining the embedded feature vector generated for the CDS of the mRNA molecule with one or more embeddings generated from the nucleotide sequences of the one or more non-coding regions of the mRNA molecule;
  processing the joint embedding using a property-prediction machine-learning model to generate an output that predicts one or more properties of the mRNA molecule, wherein the property-prediction machine-learning model has a second set of model parameters that have been updated using a second training process of a machine-learning model, wherein the second training process is based on a plurality of training examples, each training example comprising (i) a respective training input specifying a representation of a respective mRNA molecule and (ii) a respective label specifying one or more properties of the respective mRNA molecule; and
  providing the one or more predicted properties of the mRNA molecule for physically generating the mRNA molecule.

29. A system comprising:
one or more computers; and
one or more storage devices storing instructions that when executed by the one or more computers, cause the one or more computers to perform the method of claim 17.

* * * * *